US008628498B2

(12) United States Patent
Safabash et al.

(10) Patent No.: US 8,628,498 B2
(45) Date of Patent: *Jan. 14, 2014

(54) INSERTION DEVICE FOR AN INSERTION SET AND METHOD OF USING THE SAME

(75) Inventors: Jason H. Safabash, Los Angeles, CA (US); Susan M. McConnell, Woodland Hills, CA (US); Randy W. Adair, Valencia, CA (US); Jeffery V. Funderburk, Fremont, CA (US); April A. Marano, Manhattan Beach, CA (US); Jeffrey F. Field, Camarillo, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 20 days.
This patent is subject to a terminal disclaimer.

(21) Appl. No.: 13/174,123

(22) Filed: Jun. 30, 2011

(65) Prior Publication Data
US 2011/0257597 A1 Oct. 20, 2011

Related U.S. Application Data

(63) Continuation of application No. 11/687,560, filed on Mar. 16, 2007, now abandoned, which is a continuation of application No. 10/370,831, filed on Feb. 21, 2003, now Pat. No. 7,207,974, which is a continuation of application No. 09/839,052, filed on Apr. 20, 2001, now Pat. No. 6,607,509, which is a continuation-in-part of application No. 09/215,356, filed on Dec. 18, 1998, now Pat. No. 6,293,925, which is a continuation-in-part of application No. 09/002,303, filed on Dec. 31, 1997, now Pat. No. 6,093,172, which is a continuation-in-part of application No. 08/795,968, filed on Feb. 5, 1997, now Pat. No. 5,851,197.

(51) Int. Cl.
*A61B 17/34* (2006.01)

(52) U.S. Cl.
USPC ............................... 604/164.12; 604/164.01

(58) Field of Classification Search
USPC .................. 604/164.12, 164.01, 523, 164.04, 604/164.08, 164.09, 164.06, 604/164.11–164.13, 170.01, 170.02, 171
See application file for complete search history.

(56) References Cited

U.S. PATENT DOCUMENTS

| 2,577,481 A | 12/1951 | Piechaczek |
| 3,021,842 A | 2/1962 | Flood |

(Continued)

FOREIGN PATENT DOCUMENTS

| CH | 615345 A5 | 1/1980 |
| DE | 1161389 B | 1/1994 |

(Continued)

OTHER PUBLICATIONS
European Search Report for EP Application No. 02763192.8.

(Continued)

*Primary Examiner* — Emily Schmidt
*Assistant Examiner* — Michael J Anderson
(74) *Attorney, Agent, or Firm* — Medtronic MiniMed, Inc.

(57) ABSTRACT

An insertion device and insertion set. The insertion device for inserting at least a portion of at least one piercing member of an insertion set through the skin of a patient includes a device housing, a carrier body and a driver. The carrier body is slidably received within the device housing for movement between an advanced position and a retracted position. The carrier body also includes a receiving structure to support the insertion set in a position with the at least one piercing member oriented for insertion through the skin of the patient at a predetermined angle relative to the skin of the patient upon movement of the carrier body from the retracted position to the advanced position. The driver is operatively coupled between the device housing and the carrier body to urge the carrier body with a controlled force and speed from the retracted position toward the advanced position to place at least a portion of the at least one piercing member of the insertion set thorough the skin of the patient to install the insertion set to the patient. The receiving structure of the carrier body is removable from the insertion set while maintaining the installation of the insertion set to the patient.

14 Claims, 25 Drawing Sheets

(56) References Cited

U.S. PATENT DOCUMENTS

| | | | |
|---|---|---|---|
| 3,094,121 A | 6/1963 | Blumenstein et al. | |
| 3,815,605 A | 6/1974 | Schmidt et al. | |
| 3,920,001 A | 11/1975 | Edwards | |
| 4,403,989 A | 9/1983 | Christensen et al. | |
| 4,601,708 A | 7/1986 | Jordan | |
| 4,685,903 A | 8/1987 | Cable et al. | |
| 4,755,173 A | 7/1988 | Konopka et al. | |
| 4,787,891 A | 11/1988 | Levin et al. | |
| 4,883,053 A | 11/1989 | Simon | |
| 4,917,669 A * | 4/1990 | Bonaldo | 604/192 |
| 4,988,339 A * | 1/1991 | Vadher | 604/197 |
| 4,994,042 A * | 2/1991 | Vadher | 604/165.01 |
| 5,042,977 A | 8/1991 | Bechtold et al. | |
| 5,085,641 A | 2/1992 | Sarnoff et al. | |
| 5,122,119 A | 6/1992 | Lucas | |
| 5,137,516 A | 8/1992 | Rand et al. | |
| 5,141,496 A | 8/1992 | Dalto et al. | |
| 5,147,375 A | 9/1992 | Sullivan et al. | |
| 5,176,662 A | 1/1993 | Bartholomew et al. | |
| 5,241,969 A | 9/1993 | Carson et al. | |
| 5,257,980 A | 11/1993 | Van Antwerp et al. | |
| 5,259,965 A | 11/1993 | Kishi et al. | |
| 5,300,030 A | 4/1994 | Crossman et al. | |
| 5,312,254 A | 5/1994 | Rosenlicht | |
| 5,312,354 A | 5/1994 | Allen et al. | |
| 5,334,144 A | 8/1994 | Alchas et al. | |
| 5,390,671 A | 2/1995 | Lord et al. | |
| 5,391,151 A | 2/1995 | Wilmot | |
| 5,423,760 A | 6/1995 | Yoon | |
| 5,423,770 A | 6/1995 | Yoon | |
| 5,425,715 A | 6/1995 | Dalling et al. | |
| 5,478,316 A | 12/1995 | Bitdinger et al. | |
| 5,480,387 A | 1/1996 | Gabriel et al. | |
| 5,480,388 A | 1/1996 | Zadini et al. | |
| 5,568,806 A | 10/1996 | Cheney, II et al. | |
| 5,584,813 A | 12/1996 | Livingston et al. | |
| 5,586,553 A | 12/1996 | Halili et al. | |
| 5,591,188 A * | 1/1997 | Waisman | 606/182 |
| 5,599,310 A | 2/1997 | Bogert | |
| 5,643,214 A | 7/1997 | Marshall | |
| 5,665,071 A | 9/1997 | Wyrick | |
| 5,697,901 A | 12/1997 | Eriksson | |
| 5,743,880 A | 4/1998 | Hlavka | |
| 5,779,665 A | 7/1998 | Mastrototaro et al. | |
| 5,851,197 A * | 12/1998 | Marano et al. | 604/135 |
| 5,868,711 A * | 2/1999 | Kramer et al. | 604/136 |
| 5,913,869 A | 6/1999 | Reil | |
| 5,957,895 A | 9/1999 | Sage et al. | |
| 6,093,172 A * | 7/2000 | Funderburk et al. | 604/135 |
| 6,248,067 B1 | 6/2001 | Causey, III et al. | |
| 6,273,861 B1 | 8/2001 | Bates et al. | |
| 6,293,925 B1 * | 9/2001 | Safabash et al. | 604/136 |
| 6,375,627 B1 | 4/2002 | Mauze et al. | |
| 6,607,509 B2 * | 8/2003 | Bobroff et al. | 604/136 |
| 6,830,562 B2 | 12/2004 | Mogensen et al. | |
| 6,997,907 B2 * | 2/2006 | Safabash et al. | 604/157 |
| 7,207,974 B2 * | 4/2007 | Safabash et al. | 604/136 |
| 7,318,816 B2 * | 1/2008 | Bobroff et al. | 604/136 |
| 7,329,239 B2 * | 2/2008 | Safabash et al. | 604/136 |
| 2002/0022855 A1 | 2/2002 | Bobroff et al. | |
| 2002/0077599 A1 | 6/2002 | Wojcik | |
| 2002/0103476 A1 | 8/2002 | Madhani et al. | |
| 2002/0119711 A1 | 8/2002 | Van Antwerp et al. | |
| 2002/0169394 A1 | 11/2002 | Eppstein et al. | |
| 2003/0158520 A1 * | 8/2003 | Safabash et al. | 604/116 |
| 2003/0199823 A1 | 10/2003 | Bobroff et al. | |
| 2004/0002682 A1 * | 1/2004 | Kovelman et al. | 604/136 |
| 2007/0156094 A1 * | 7/2007 | Safabash et al. | 604/164.12 |
| 2011/0040256 A1 | 2/2011 | Bobroff et al. | |
| 2011/0257597 A1 * | 10/2011 | Safabash et al. | 604/164.12 |

FOREIGN PATENT DOCUMENTS

| | | |
|---|---|---|
| DE | 29605069 U1 | 8/1996 |
| EP | 0615768 B1 | 12/1999 |
| GB | 943680 A | 12/1963 |
| GB | 1519434 A | 7/1978 |
| WO | 9521645 A1 | 8/1995 |
| WO | 9640324 A1 | 12/1996 |
| WO | 98/33549 A1 | 8/1998 |
| WO | 99/33504 A1 | 7/1999 |
| WO | 02081012 A2 | 10/2002 |
| WO | 02100457 A2 | 12/2002 |
| WO | 02100457 A3 | 12/2002 |

OTHER PUBLICATIONS

European Search Report for EP Application No. 98904865.7.
PCT International Search Report for Application No. PCT/US02/10271.
PCT International Search Report for Application No. PCT/US98/26978.

* cited by examiner

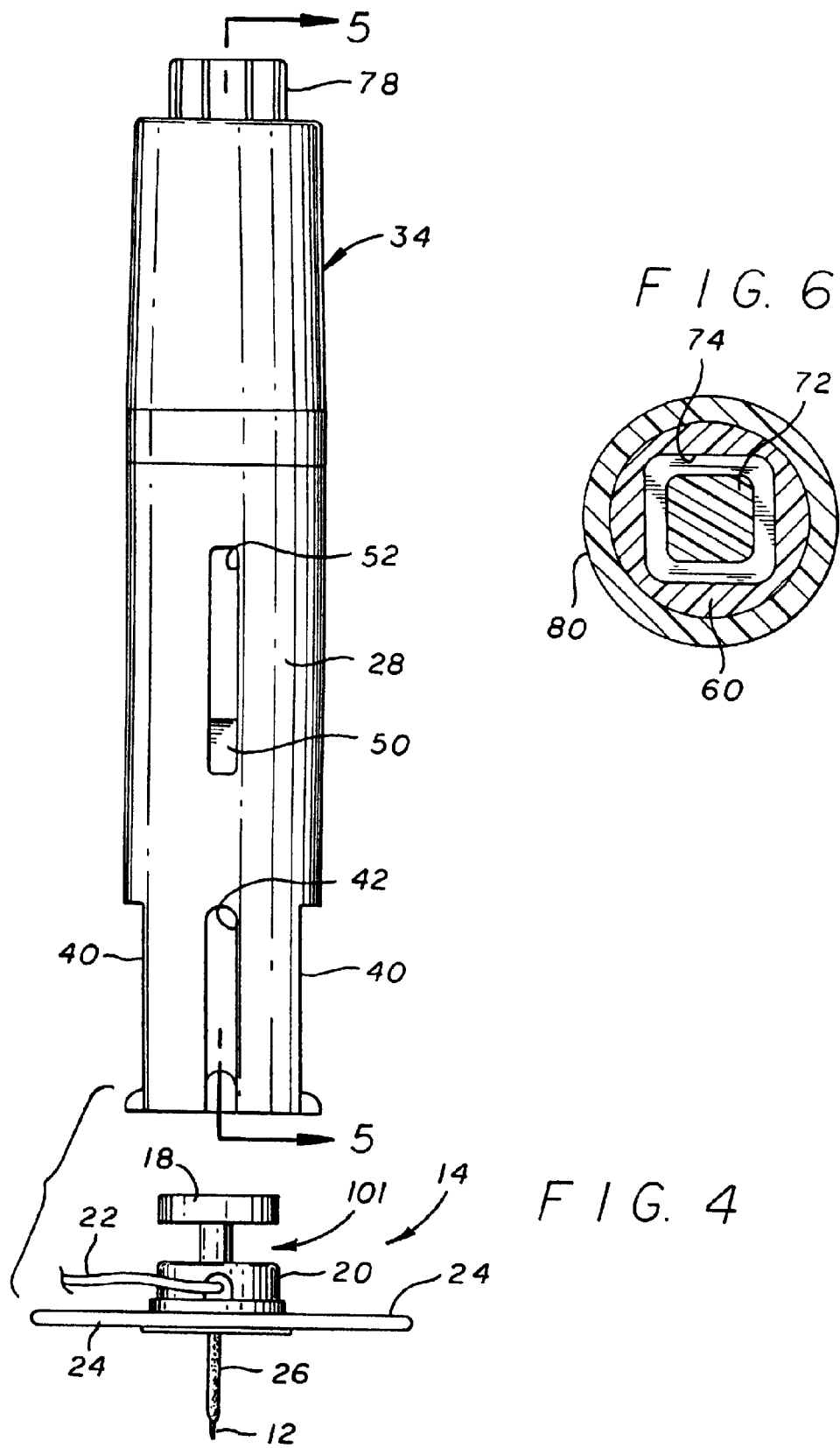

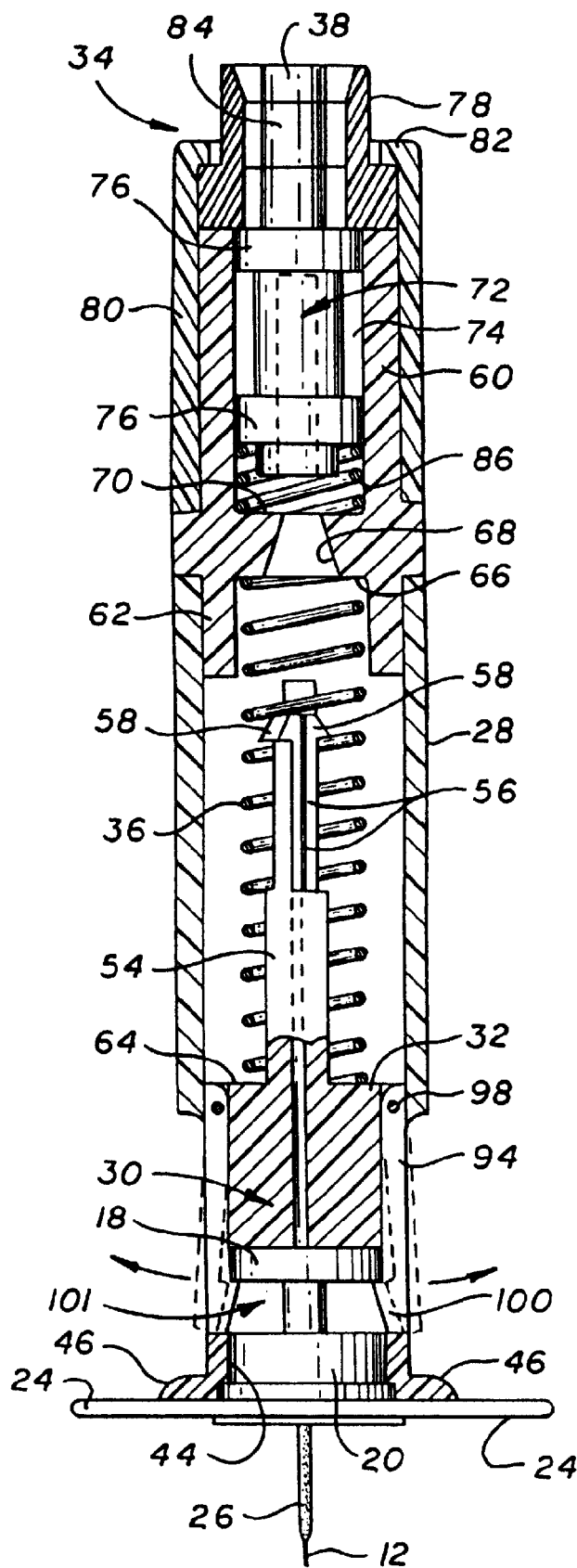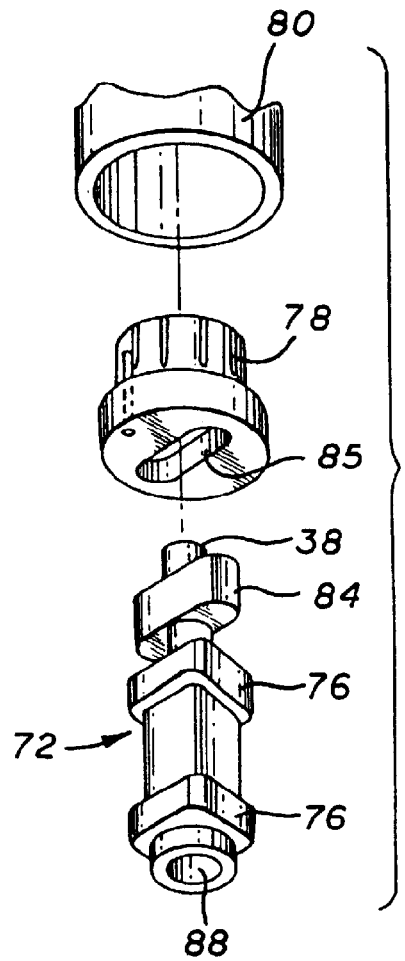
FIG. 7
FIG. 8

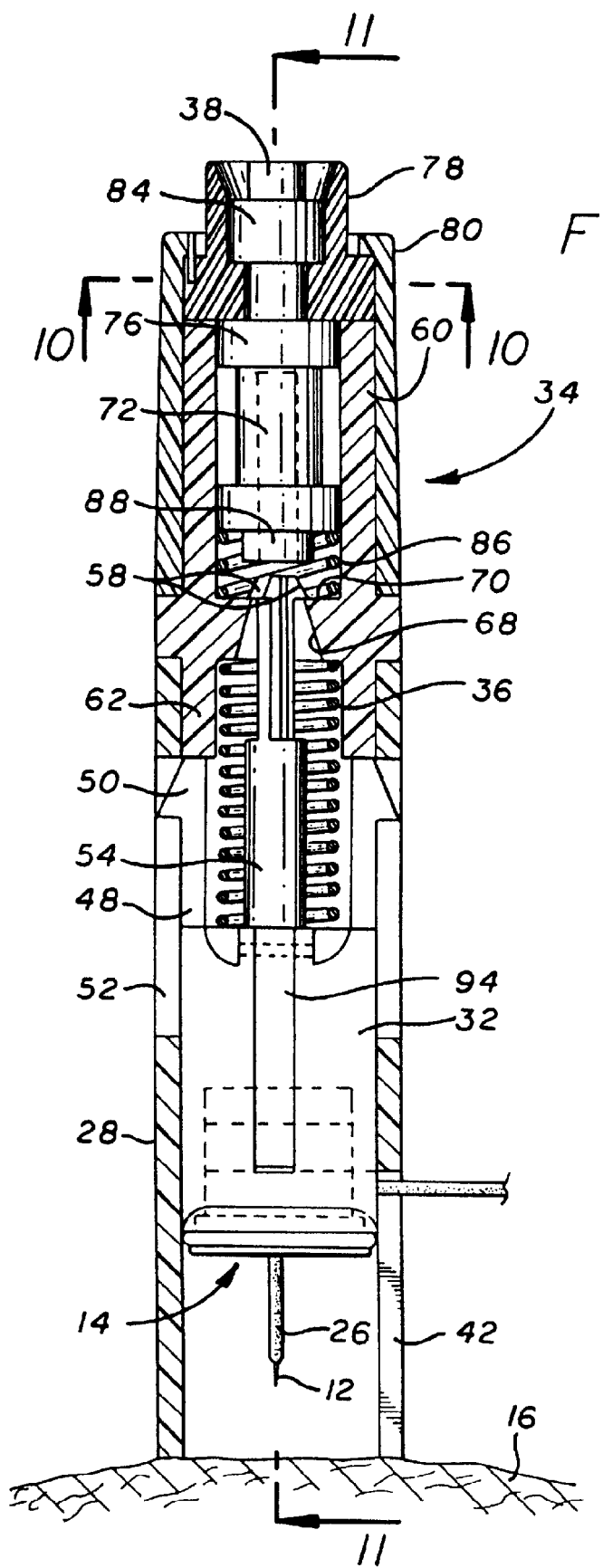
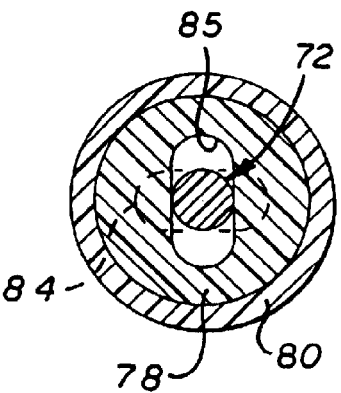
FIG. 9
FIG. 10

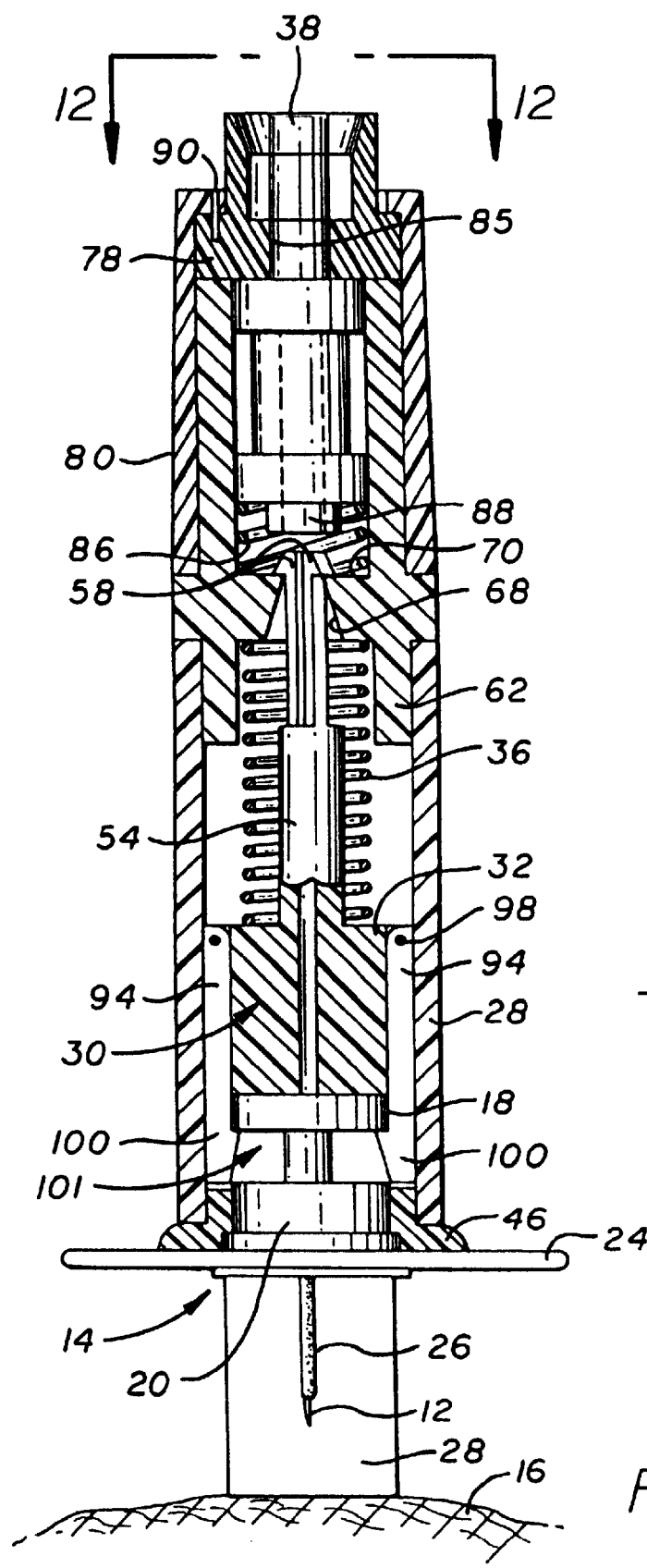
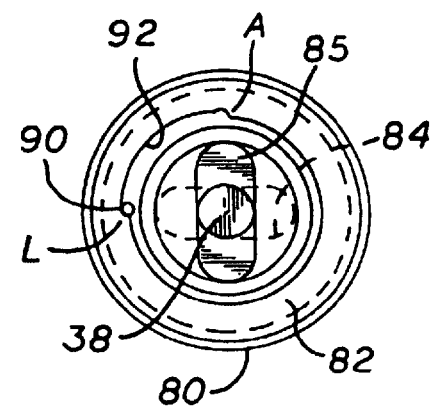
FIG. 12
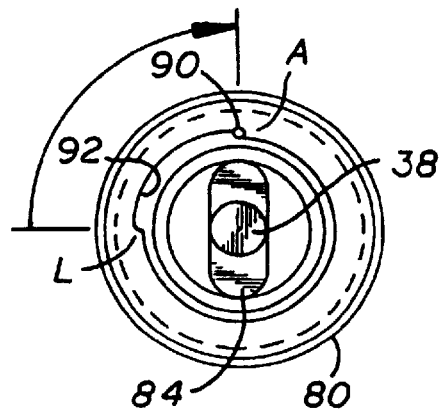
FIG. 14
FIG. 11

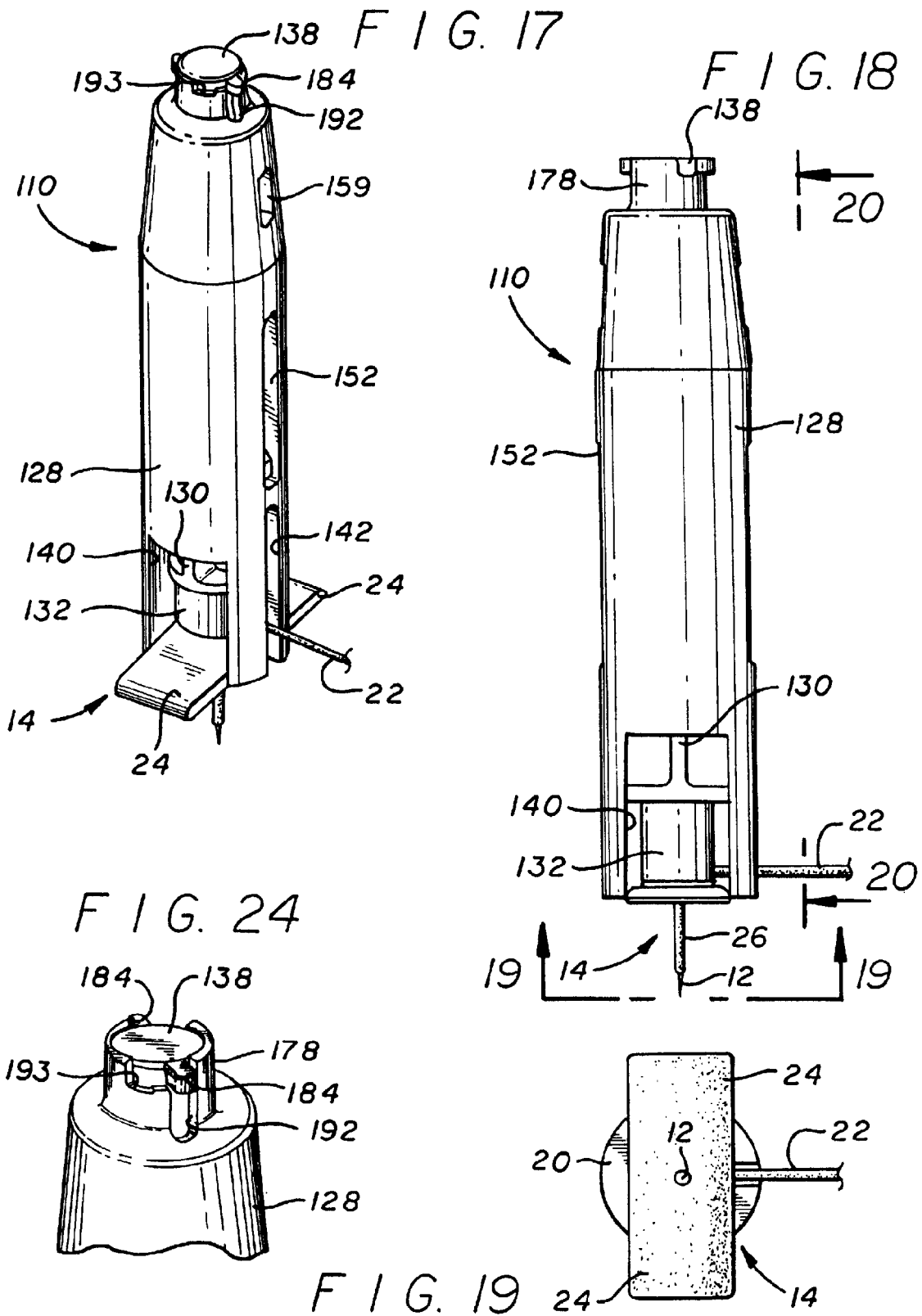

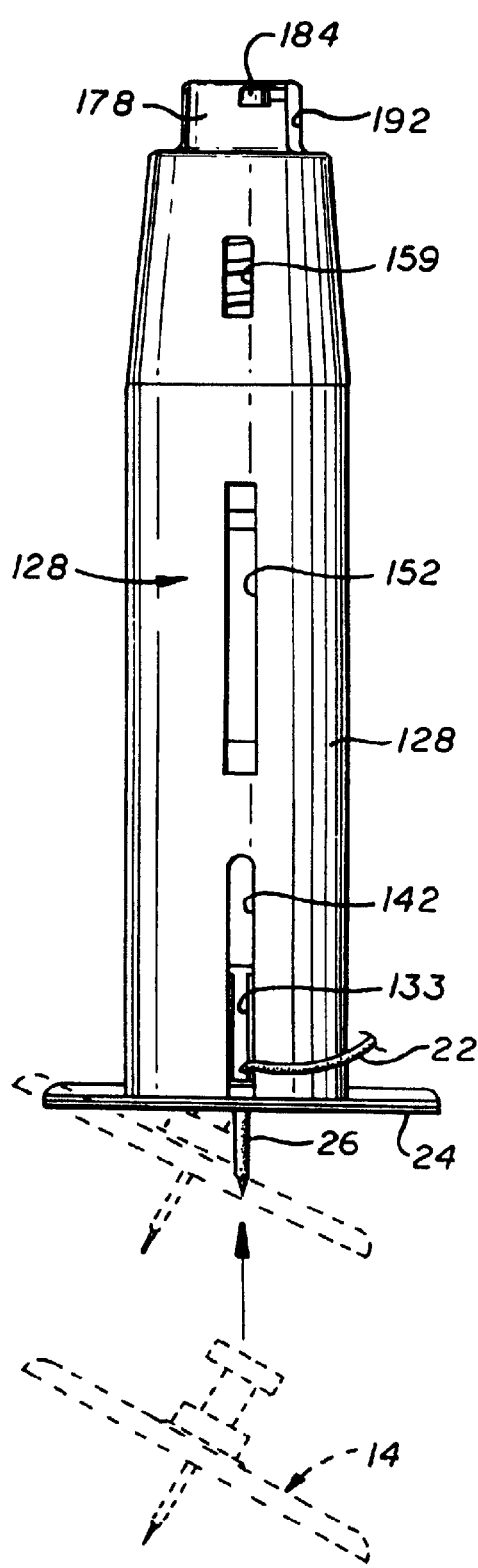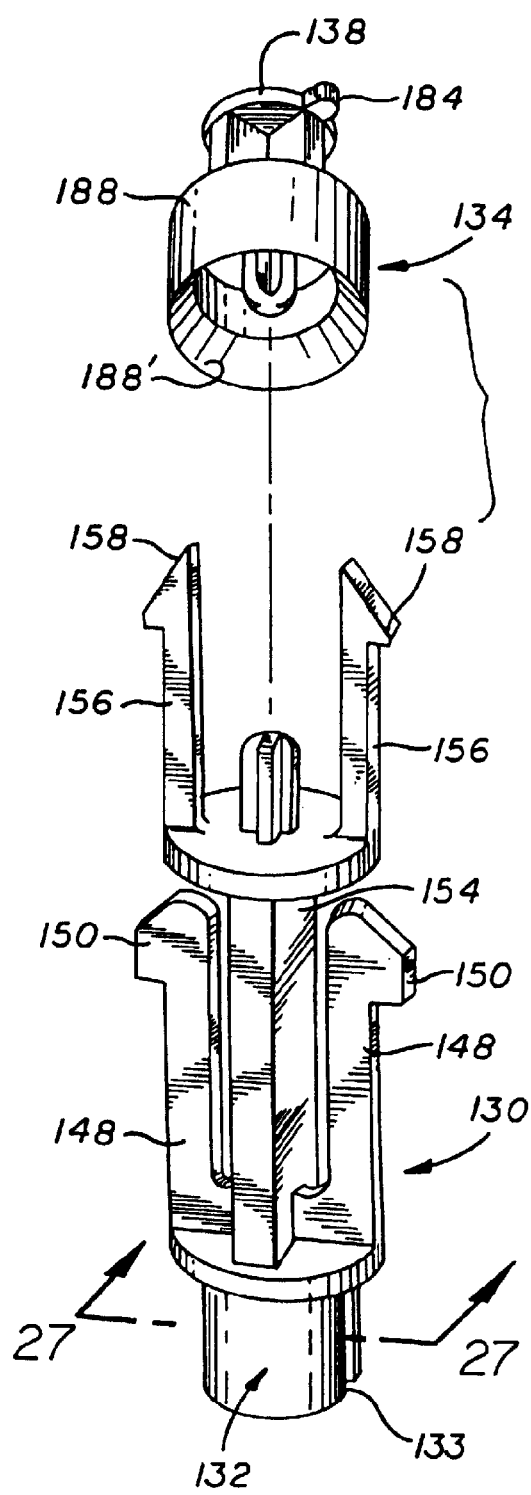

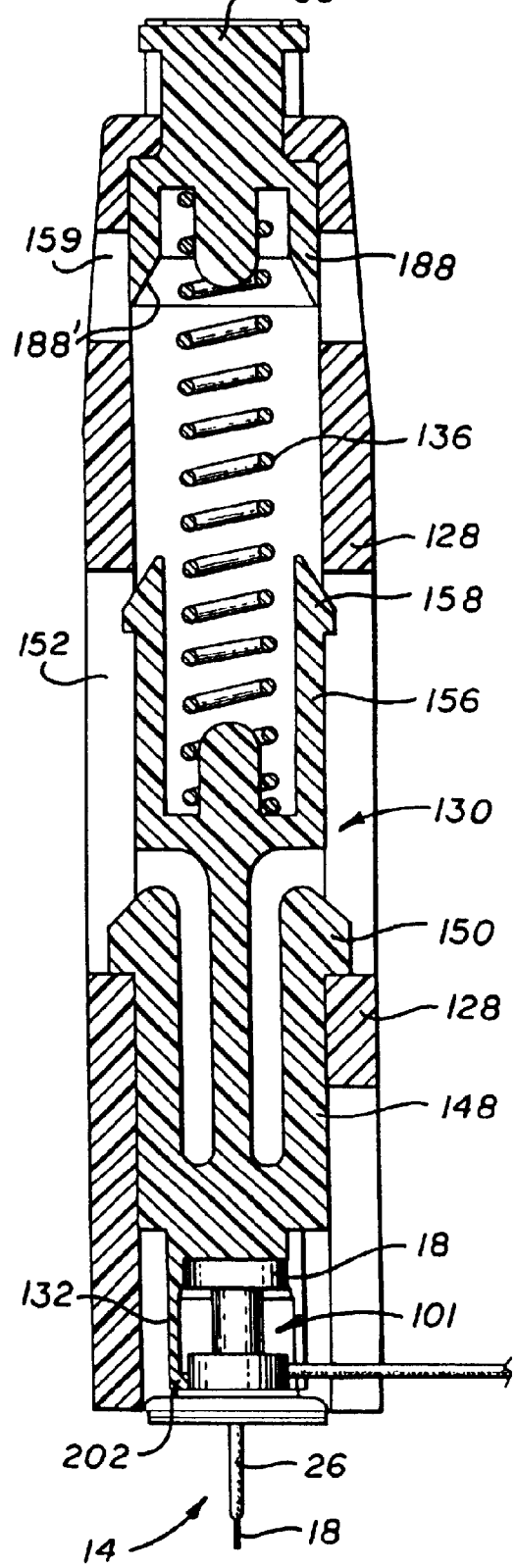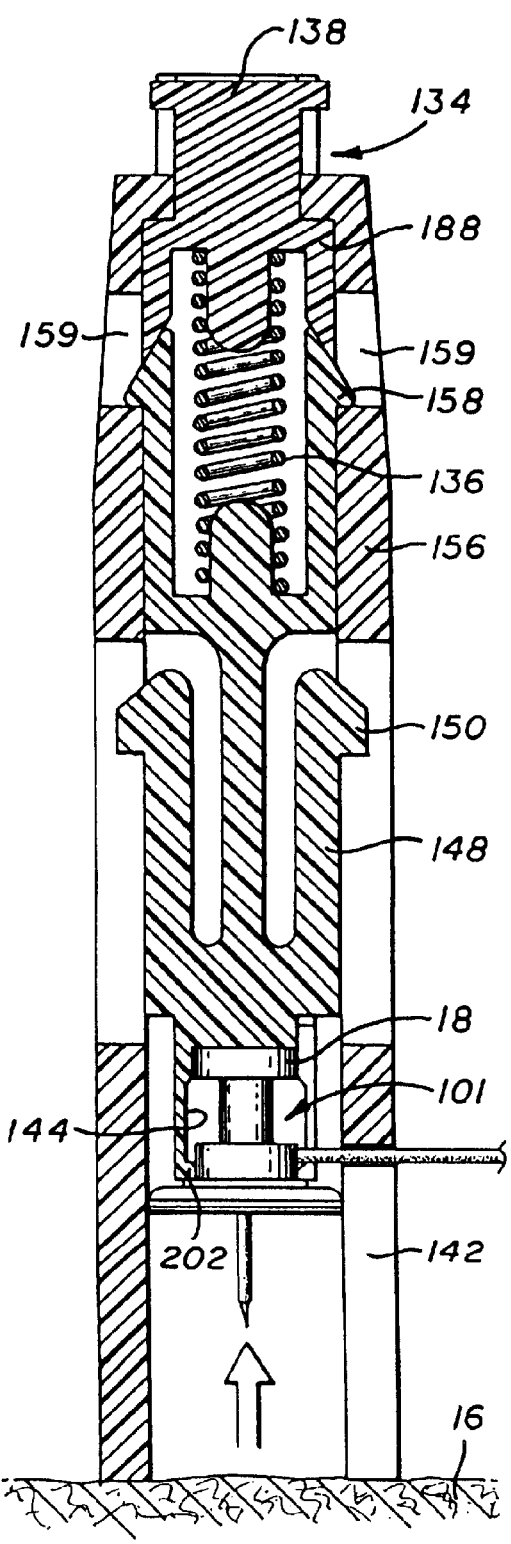

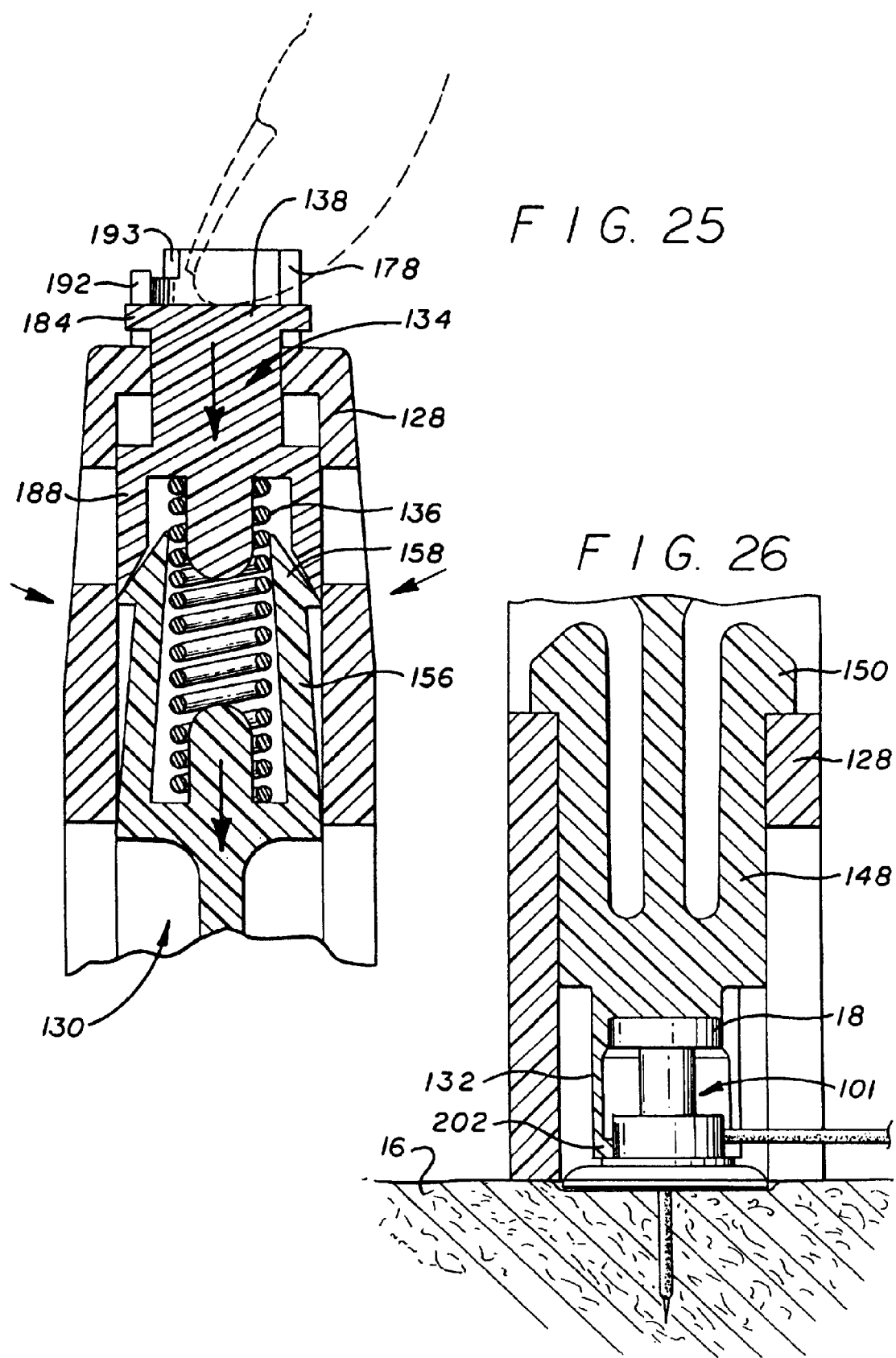

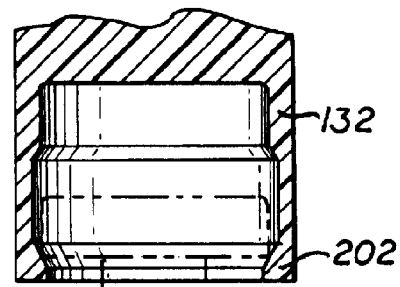
FIG. 27
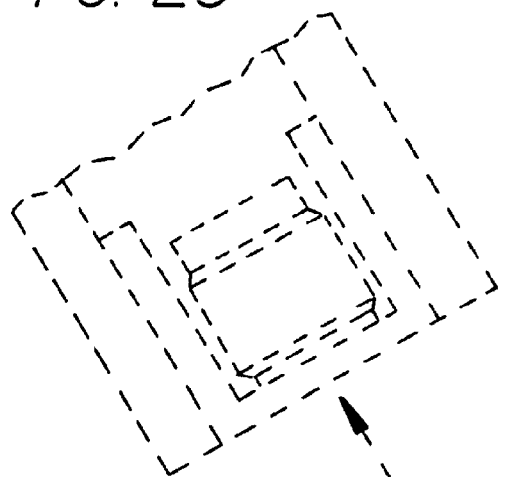
FIG. 29
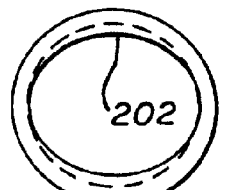
FIG. 28
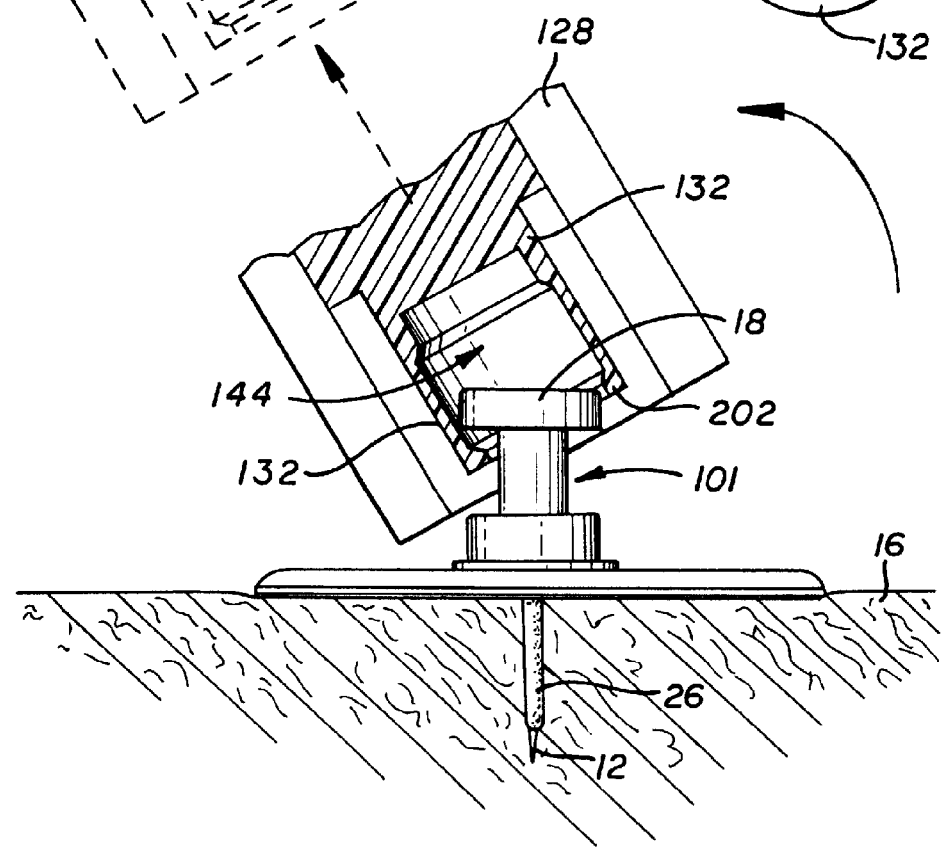

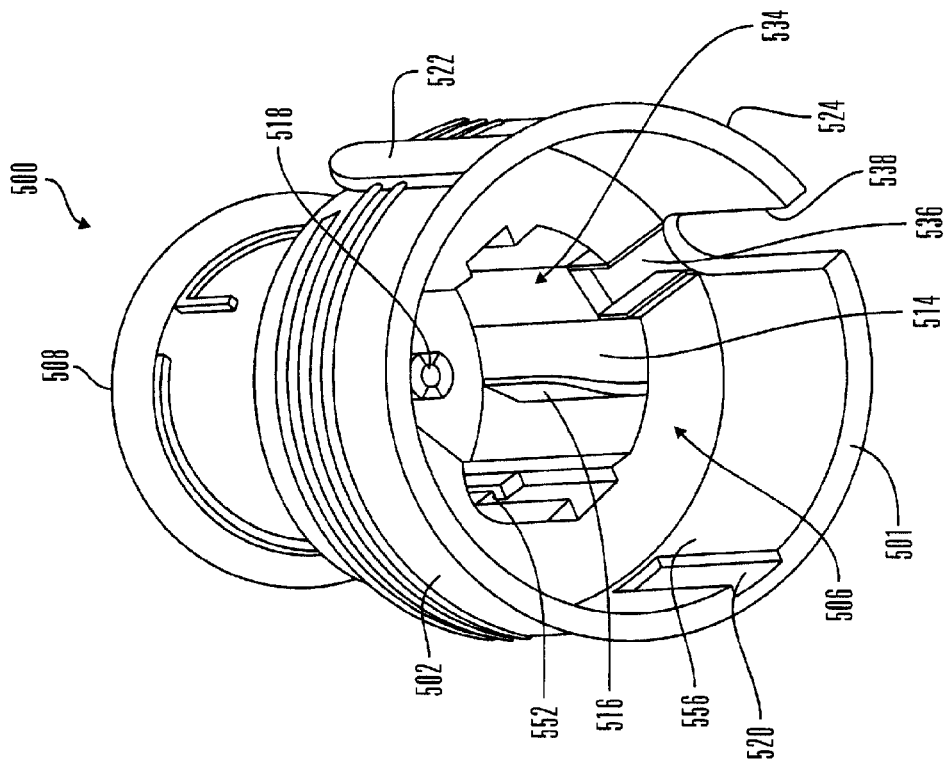
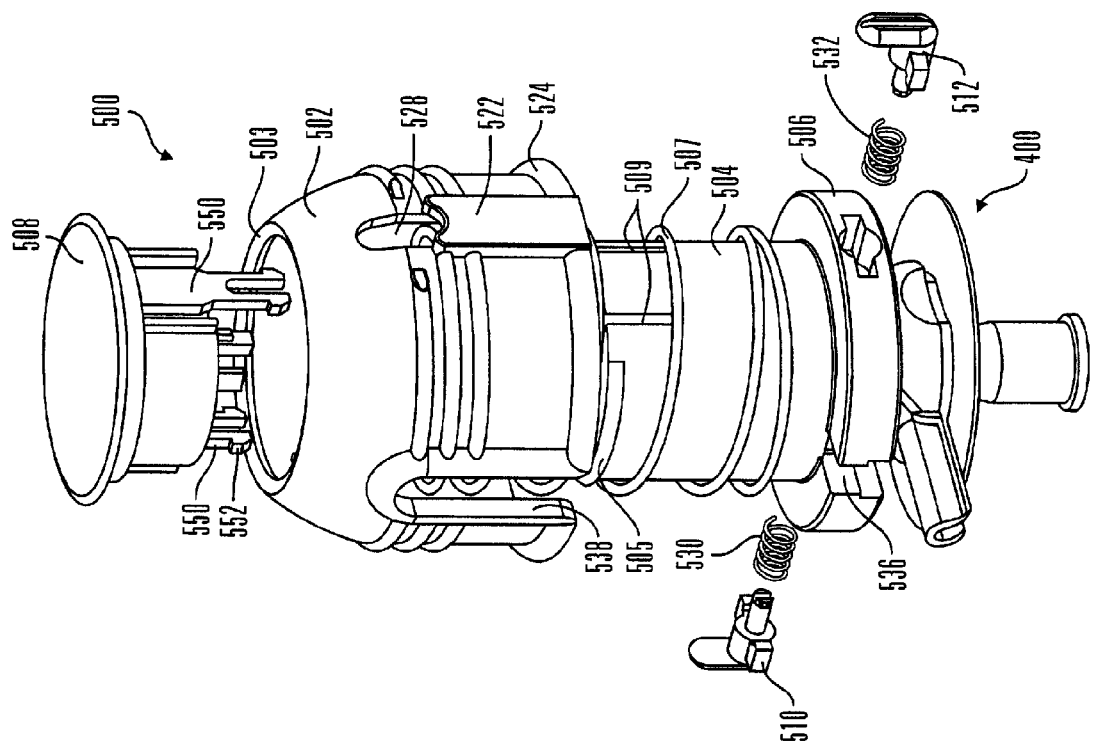

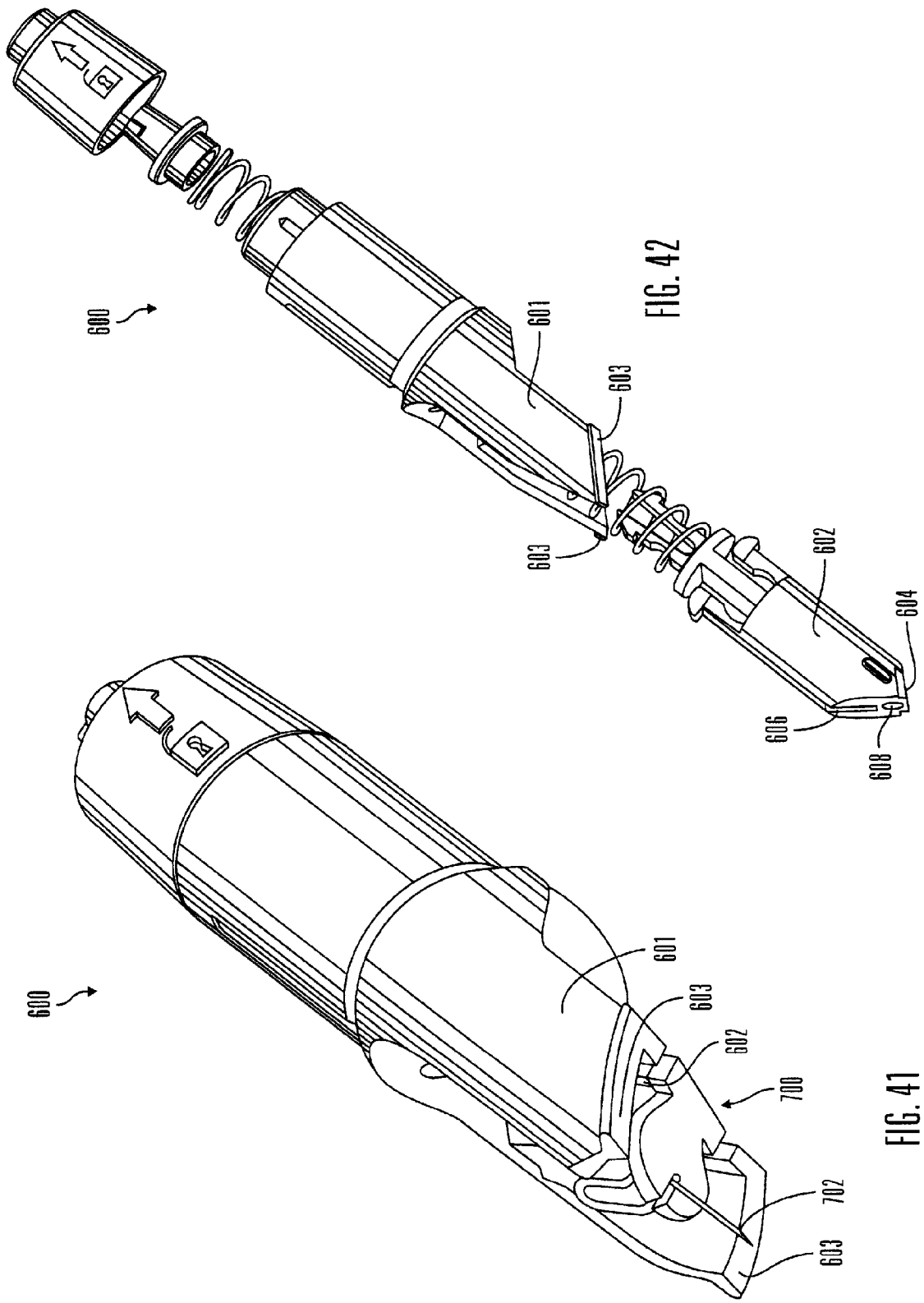

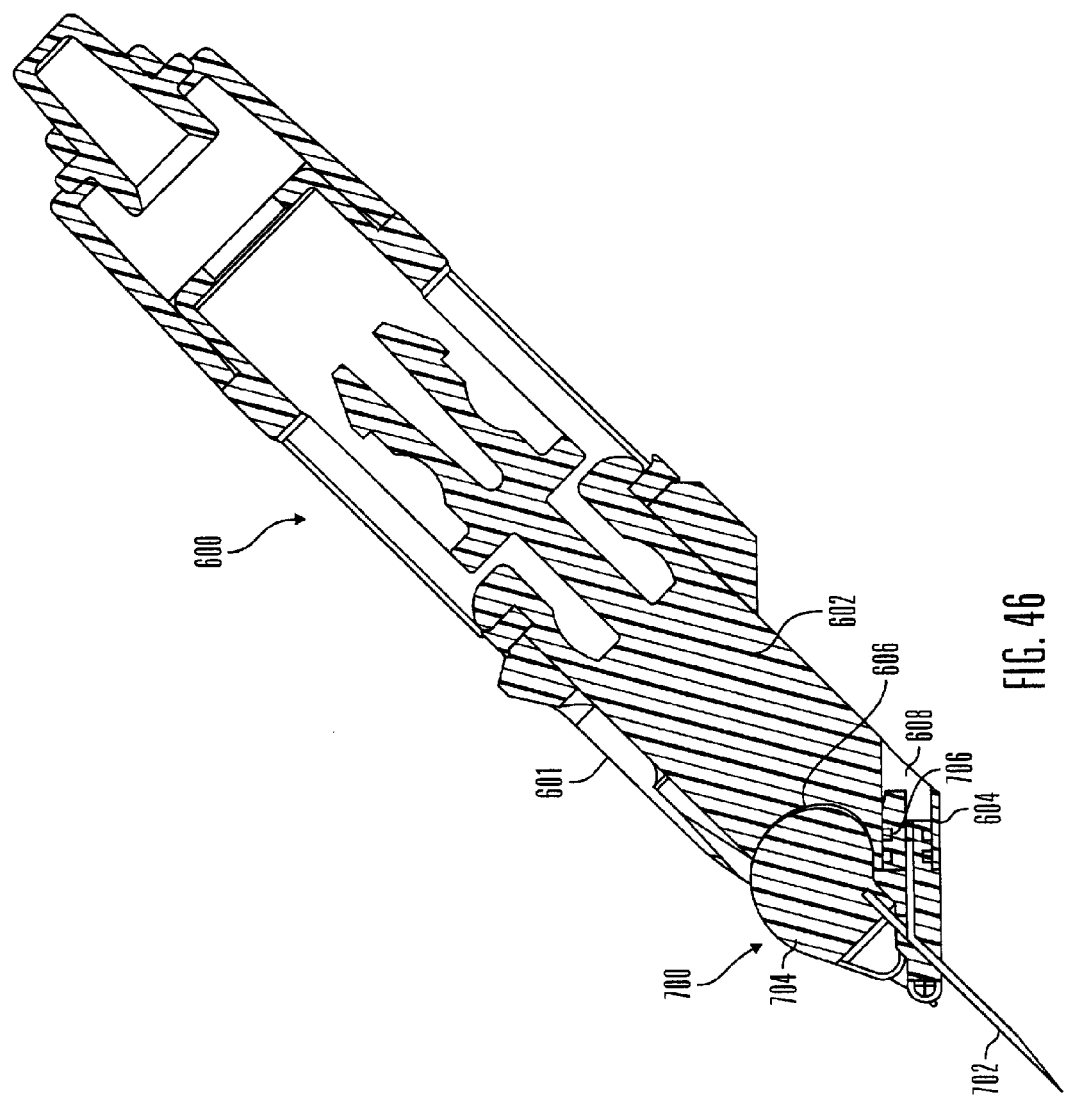
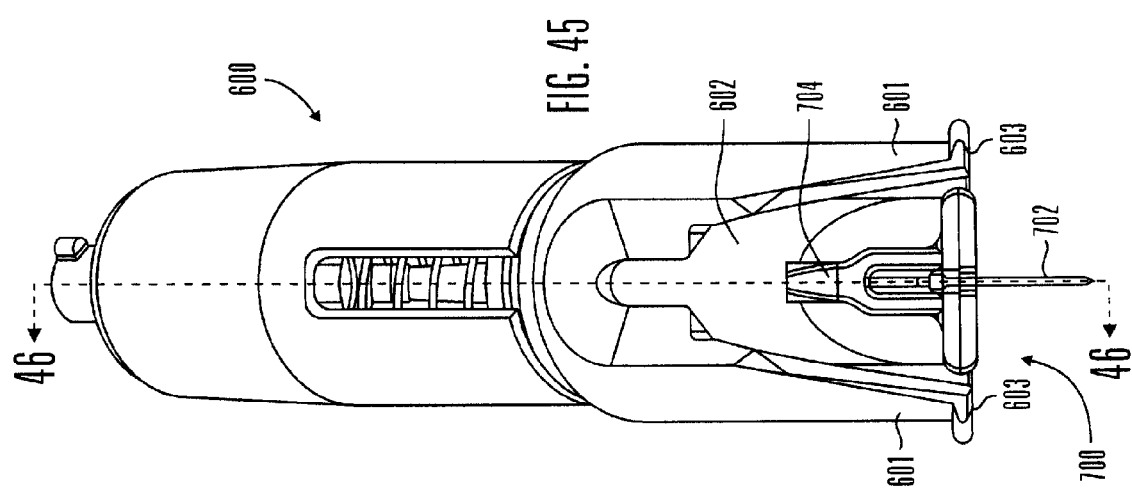

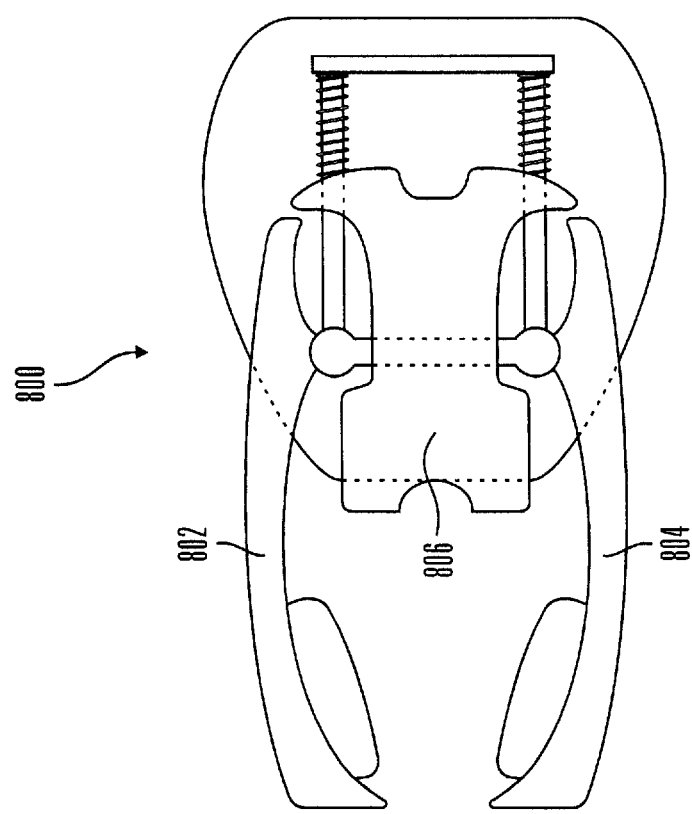

INSERTION DEVICE FOR AN INSERTION SET AND METHOD OF USING THE SAME

RELATED APPLICATIONS

This is a continuation application of U.S. patent application Ser. No. 11/687,560 filed on Mar. 16, 2007 now abandoned which was a continuation application of U.S. patent application Ser. No. 10/370,831 filed on Feb. 21, 2003 now U.S. Pat. No. 7,207,974, which is a continuation application of U.S. patent application Ser. No. 09/839,052 filed on Apr. 20, 2001, now U.S. Pat. No. 6,607,509, which is a continuation-in-part application of U.S. patent application Ser. No. 09/215,356 filed on Dec. 18, 1998, now U.S. Pat. No. 6,293,925, which is a continuation-in-part application of U.S. patent application Ser. No. 09/002,303 filed on Dec. 31, 1997, now U.S. Pat. No. 6,093,172, which is a continuation-in-part application of U.S. patent application Ser. No. 08/795,968 filed on Feb. 5, 1997, now U.S. Pat. No. 5,851,197, all of which are specifically incorporated by reference herein.

FIELD OF THE INVENTION

This invention relates generally to an insertion device for automatic placement of an insertion set through the skin of a patient, and in particular embodiments to a compact and easily operated insertion device for placement of an insertion needle of a subcutaneous insertion set or the like through the skin of a patient with a controlled force and insertion speed by the patient.

BACKGROUND OF THE INVENTION

Medical needles are widely used in the course of patient care and treatment, particularly with respect to the delivery of selected medications to a patient. In one common form, hollow hypodermic needles are employed for transcutaneous delivery of a selected medication from a syringe or the like. In another common form, insertion needles are employed for transcutaneous placement of a soft and relatively flexible tubular cannula, followed by insertion needle removal and subsequent infusion of medical fluid to the patient through the cannula. More recently, insertion needles have also been used for transcutaneously placing other medical devices such as a subcutaneous sensor for monitoring specified patient parameters, such as blood glucose level.

In certain medical treatment regimens, it may be necessary or desirable for the patient to transcutaneously place the medical needle. For example, diabetic patients frequently self-administer insulin injections or periodically place a subcutaneous insertion with a cannula for subsequent programmable delivery of insulin by means of a medication infusion pump of the general type described in U.S. Pat. No. 4,685,903. Such subcutaneous insertion sets are disclosed, for example, in U.S. Pat. Nos. 4,755,173; 5,176,662; and 5,257,980 which are incorporated by reference herein. Diabetic patients may also use a subcutaneous insertion set to periodically place a transcutaneous glucose sensor wherein such sensor insertion sets are disclosed, for example, In U.S. Pat. Nos. 5,390,674; 5,568,806; 5,586,553, which are also incorporated by reference herein.

Some patients are reluctant or hesitant to pierce their own skin with a medical needle, and thus encounter difficulties in correct needle placement for proper administration of the medication. Such difficulties can be attributable to insufficient manual dexterity or skill to achieve proper needle placement or, alternately to, anxiety associated with anticipated discomfort as the needle pierces the skin. This problem can be especially significant with medications delivered via a subcutaneous flexible insertion set, since incorrect placement can cause kinking of the cannula and resultant obstruction of medication flow to the patient. Cannula kinking can be due to insertion set placement at an incorrect angle relative to the patient's skin, and/or needle placement with an incorrect force and speed of insertion.

The present invention relates to an automatic injector, particularly for use with a subcutaneous insertion set, for quickly and easily placing an insertion needle through the skin of a patient at the correct insertion angle, and with a speed and force of insertion which minimizes patient discomfort.

SUMMARY OF THE DISCLOSURE

It is an object of an embodiment of the present invention to provide an improved insertion device and insertion set, which obviates for practical purposes, the above mentioned limitations.

According to an embodiment of the invention, an injector is provided for quick and easy transcutaneous placement of a medical needle through the skin of a patient, particularly such as an insertion of a subcutaneous insertion set. The injector is designed to place the needle through the skin at a selected insertion angle and with a controlled force and speed of insertion, to ensure proper needle placement with minimal patient discomfort. The injector is particularly designed to meet these objectives, while safeguarding against undesired projection of the medical needle through free space, in the event that the injector is actuated in spaced relation to the patient's skin.

The injector comprises a spring-loaded plunger having a head for receiving and supporting an insertion set in a position with an insertion projecting outwardly for transcutaneous placement through the skin of a patient. The plunger is designed for retraction and retention within a barrel to a cocked position with a drive spring compressed in a manner applying a predetermined spring force to the plunger head. A front or nose end of the injector barrel is designed for pressed placement against the skin of a patient, at a selected needle insertion site, and in an orientation with the needle disposed at a correct or desired insertion angle. A trigger member is operable to release the plunger and thereby permit the drive spring to carry the insertion set toward the patient's skin with a controlled force and speed, resulting in proper transcutaneous placement of the insertion needle with minimal patient discomfort.

The plunger head includes a safety lock mechanism to retain the insertion set against projection from the injector barrel. In one preferred form, the safety lock mechanism comprises at least one and preferably a pair of safety lock arms for engaging and retaining the insertion set when the plunger is retracted from a fully advanced position. Each safety lock arm includes a cam lobe for engaging an appropriately shaped recess on the insertion set to prevent release thereof from the plunger head, unless and until the plunger head is returned to the fully advanced position. In such fully advanced position, the shape of the cam lobe permits quick and easy separation of the injector from the insertion set with a minimal separation force.

In operation, the safety lock arms thus prevent projection of the insertion set from the injector, in the event that the trigger member is actuated with the nose end of the barrel spaced from the skin of a patient. In that event, the plunger head is advanced with the controlled force and speed to the fully advanced position, but the insertion set is not thrown from the injector as a projectile. Instead, the insertion set travels rapidly with the plunger head to the fully advanced position, whereat the injector can be separated with minimal separation force from the insertion set.

In an alternative preferred form, the safety lock mechanism comprises a plunger head having a cylindrical shape defining a forwardly open cavity for receiving and supporting an insertion set with the insertion needle and cannula projecting outwardly. In this embodiment, the plunger head includes a radially inwardly projecting rim at a forward or nose end thereof, wherein the rim defines an oval-shaped opening. The size of the rim opening permits relatively free reception of a hub on the insertion set, with the infusion set oriented at an angle relative to a central axis of the plunger head and barrel. The insertion set is then reoriented to align the insertion needle coaxially with the central axis of the barrel and plunger head, so that the rim is received into a recess on the insertion set and functions to retain the infusion set against undesired release from the injector during spring-driven placement of the needle. After needle placement, the injector is released from the insertion set with minimal separation force by orienting the injector angularly relative to the insertion set to permit free slide out passage of the hub through the oval rim opening.

In a further alternative form of the invention, the plunger head is shaped to define a laterally open undercut slot sized for relatively free slide-fit reception of the needle hub of the insertion set. In this version, the insertion set is assembled quickly and easily with the plunger head of the injector by laterally sliding the hub into the laterally open slot, thereby orienting the medical needle generally coaxially relative to the central axis of the injector barrel and plunger head. In this position, the plunger head can be retracted and locked, followed by appropriate trigger member release for transcutaneously placing the medical insertion needle. After the needle is placed on the patient, the injector can be disassembled from the insertion set by laterally sliding the injector relative to the needle hub. Alternatively, the injector can be withdrawn or retracted from the patient's skin to slidably separate the needle from the insertion set which remains in place on the patient's skin.

In other embodiments of the present invention, an insertion device for inserting at least a portion of at least one piercing member of an insertion set through the skin of a patient includes a device housing, a carrier body and a driver. The carrier body is slidably received within the device housing for movement between an advanced position and a retracted position. The carrier body also includes a receiving structure to support the insertion set in a position with the at least one piercing member oriented for insertion through the skin of the patient at a predetermined angle relative to the skin of the patient upon movement of the carrier body from the retracted position to the advanced position. The driver is operatively coupled between the device housing and the carrier body to urge the carrier body with a controlled force and speed from the retracted position toward the advanced position to place at least a portion of the at least one piercing member of the insertion set thorough the skin of the patient to install the insertion set to the patient. The receiving structure of the carrier body is removable from the insertion set while maintaining the installation of the insertion set to the patient.

In particular embodiments, the predetermined angle relative to the skin is about 90 degrees, between 90 degrees and 10 degrees, or is after insertion between 0 and 10 degrees. In additional embodiments, the insertion set is a transcutaneous insertion set, a subcutaneous insertion set, an infusion set, sensor set or the like. In still other embodiments, the insertion set rests mainly on the surface of the skin after insertion or the insertion set is implanted in the skin of the patient. In preferred embodiments, the at least one piercing member is a needle. In alternative embodiments, the at least one piercing member is a plurality of needles, and can also be a plurality of micro-needles. Also, in some embodiments, the insertion set insertion set can be both an infusion set and a sensor set combined into an integral unit.

In yet other embodiments the insertion device, the device housing has a forward end defining a generally planar angled insertion contact surface for placement against the skin of a patient with the device housing in a predetermined orientation relative to the patient's skin that mirrors the predetermined angle relative to the skin of the patient. Other embodiments include a trigger mechanism that actuates the driver. For instance, the trigger mechanism includes at least one trigger for fingertip depression to actuate the driver for movement of the carrier body from the retracted position to the advanced position. In addition, the driver can include at least one spring for spring-loaded movement of the carrier body from the retracted position to the advanced position. Further, the driver can include a force changing mechanism that permits alteration of the controlled force and speed of the carrier body moving from the retracted position to the advanced position from one insertion cycle to another insertion cycle. In still further embodiments, the device housing and the carrier body include a cooperatively engageable track mechanism for guiding movement of the carrier body between the advanced and retracted positions while retaining the carrier body against rotation relative to the device housing.

In additional embodiments of the insertion device, the at least one piercing member is provided with a piercing member hub as part of the insertion set. In addition, the receiving structure of the carrier body includes a recess formed therein for mated slide-fit reception of the piercing member hub of the insertion set. Further, the recess of the receiving structure can include a laterally open undercut recess. Alternatively, the receiving structure may include a safety retainer structure that retains the at least one piercing member on the receiving structure during movement from the retracted position to the advanced position. This safety retainer structure permits separation of the at least one piercing member from the carrier body when the carrier body is in the advanced position.

Yet another embodiment of the present invention is directed to an insertion set for insertion through the skin of a patient by an insertion device. The insertion device has a slidable carrier body for movement between an advanced position and a retracted position. The carrier body of the insertion device including a receiving structure to support the insertion set in a position for insertion through the skin of the patient upon movement of the carrier body from the retracted position to the advanced position. The insertion device also having a driver operatively coupled to the carrier body that urges the carrier body with a controlled force and speed from the retracted position toward the advanced position for insertion of the insertion set thorough the skin of the patient. The insertion set includes at least one piercing member and a set housing. The at least one piercing member includes a portion of the at least one piercing member that is insertable through the skin of the patient. The set housing is coupled to the at least one piercing member. Also, the set housing is shaped to fit within the carrier body of the insertion device to orient the at least one piercing member for placement through the skin of the patient of at least a portion of the at least one piercing member at a predetermined angle relative to the skin of the patient to install the insertion set to the patient. The set housing of the insertion set is removable from the receiving structure of the carrier body while maintaining the installation of the insertion set to the patient.

In particular embodiments of the insertion set, the predetermined angle relative to the skin is about 90 degrees, between 90 degrees and 10 degrees, or is after insertion between 0 and 10 degrees. In additional embodiments, the insertion set is a transcutaneous insertion set, a subcutaneous insertion set, an infusion set, sensor set or the like. In still other embodiments, the insertion set rests mainly on the surface of the skin after insertion or the insertion set is implanted in the skin of the patient. In preferred embodiments, the at least one piercing member is a needle. In alternative embodiments, the at least one piercing member is a plurality of needles, and can also be a plurality of micro-needles. Also, in some embodiments, the insertion set can be both an infusion set and a sensor set combined into an integral unit.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 4 is an enlarged exploded perspective view illustrating assembly of the injector with a subcutaneous insertion set;

FIG. 6 is a transverse sectional view taken generally on the line 6-6 of FIG. 5;

FIG. 7 is an enlarged longitudinal sectional view taken generally on the line 7-7 of FIG. 2;

FIG. 8 is an enlarged and exploded fragmented perspective view illustrating a trigger assembly for use in the injector;

FIG. 9 is a longitudinal sectional view similar to FIG. 5, and showing the injector with insertion set received therein for transcutaneous placement through the skin of a patient;

FIG. 10 is a transverse sectional view taken generally on the line 10-10 of FIG. 9;

FIG. 11 is a longitudinal sectional view taken generally on the line 11-11 of FIG. 9;

FIG. 12 is a rear end elevation view taken generally on the line 12-12 of FIG. 11, and depicting the trigger assembly in a locked position;

FIG. 14 is a rear end elevation view taken generally on the line 14-14 of FIG. 13, similar to FIG. 12, but showing the trigger assembly in an unlocked position;

FIG. 17 is a perspective view depicting an alternative preferred form of the invention;

FIG. 18 is a front elevation view of the injector shown in FIG. 17;

FIG. 19 is a front or nose end view of the injector, taken generally on the line 19-19 of FIG. 18;

FIG. 20 is an enlarged side elevation view of the injector, taken generally on the line 20-20 of FIG. 19;

FIG. 21 is a further enlarged longitudinal sectional view taken generally on the line 21-21 of FIG. 17;

FIG. 22 is an enlarged exploded perspective view illustrating construction details of a plunger and trigger member for use in the injector of FIG. 17;

FIG. 23 is an enlarged longitudinal sectional view similar to FIG. 21, and depicting the injector with the trigger member in a cocked position;

FIG. 24 is a fragmented perspective view showing the upper end of the injector depicted in FIG. 23, with the trigger member in the cocked position;

FIG. 25 is an enlarged and fragmented longitudinal sectional view illustrating actuation of the trigger member;

FIG. 26 is an enlarged and fragmented longitudinal sectional view showing the plunger in a fully advanced position with the infusion set placed on the patient's skin;

FIG. 27 is an enlarged fragmented longitudinal sectional view taken generally on the line 27-27 of FIG. 22, and depicting a portion of the plunger;

FIG. 28 is a front or nose end elevational view of the plunger, taken generally on the line 28-28 of FIG. 27; and FIG. 29 is an enlarged fragmented longitudinal sectional view illustrating release of the injector from an infusion set placed on the patient's skin;

FIG. 35 is a perspective view of an insertion device with one type of an insertion set in accordance with a second embodiment of the present invention.

FIG. 36 is a bottom perspective view of the insertion device of FIG. 35.

FIG. 41 is a perspective view of an insertion device with one type of an insertion set in accordance with a third embodiment of the present invention.

FIG. 42 is an exploded perspective view of the insertion device shown in FIG. 41.

FIG. 45 is a front perspective view of the insertion device and the one type of insertion set shown in FIG. 41.

FIG. 46 is a cross-sectional view of the insertion device and the one type of insertion set as shown along the line 46-46 in FIG. 45.

FIG. 47 is a top schematic view of an insertion device in accordance with a fourth embodiment of the present invention.

DETAILED DESCRIPTION OF THE PREFERRED EMBODIMENTS

Figure 1:
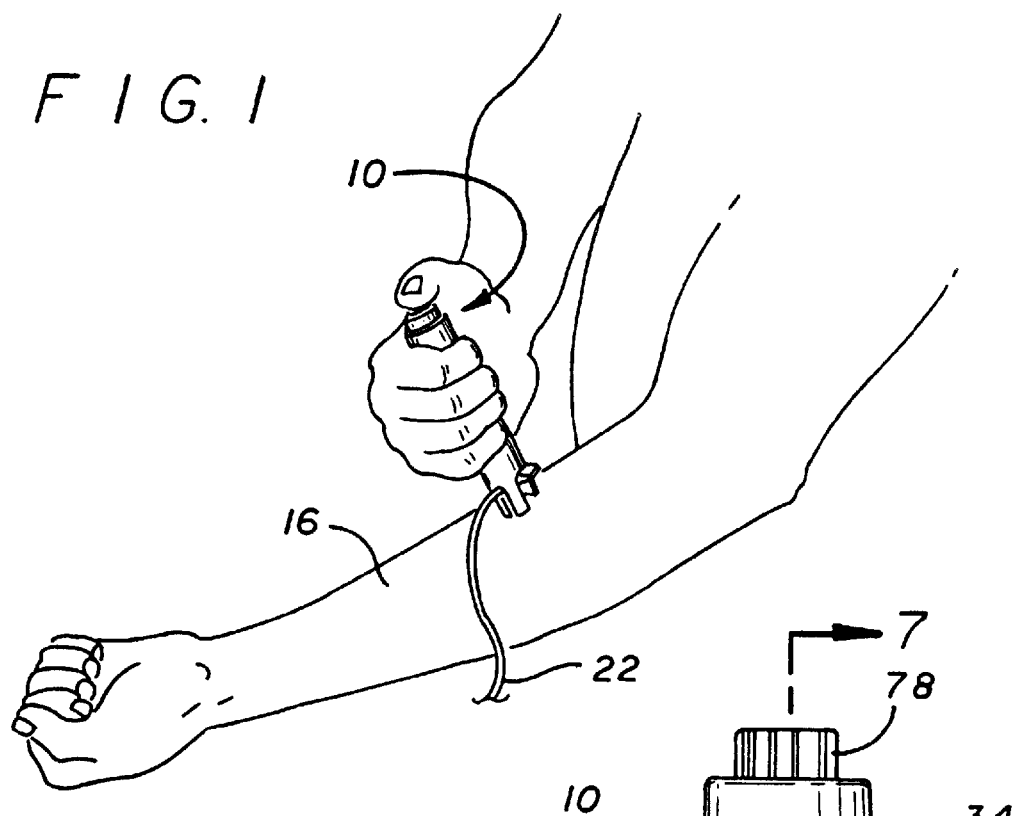
FIG. 1 is a perspective view illustrating use of an automatic injector embodying the novel features of the invention.
Figure 3:
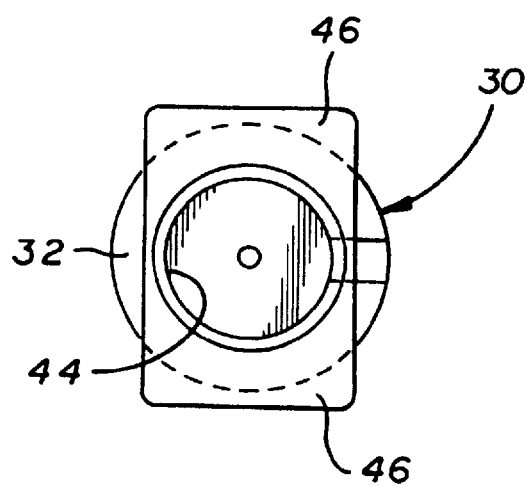
FIG. 3 is a front or nose end view of the injector, taken generally on the line 3-3 of FIG. 2.
Figure 2:
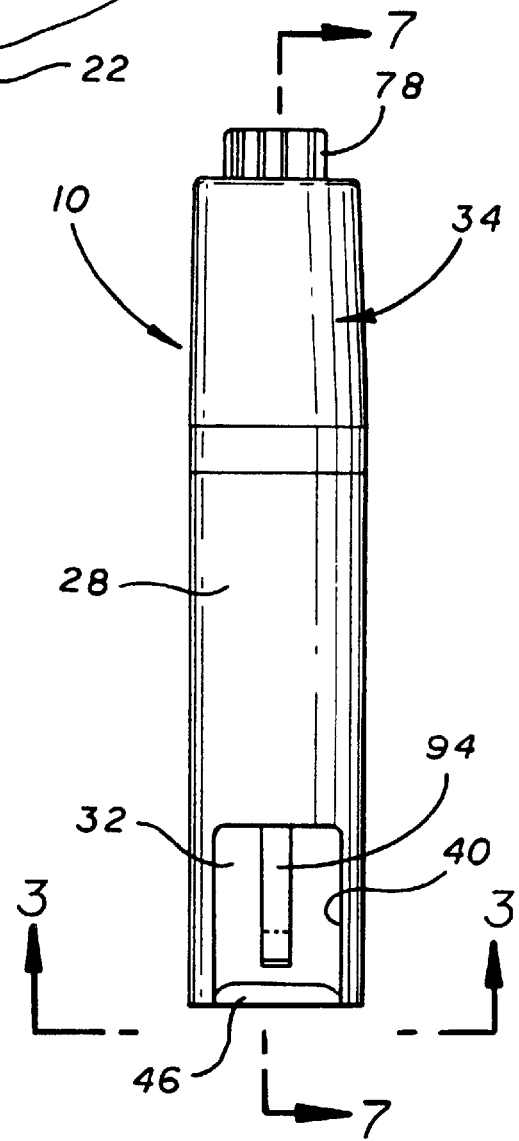
FIG. 2 is an enlarged front elevation view of the injector shown in FIG. 1.

As shown in the drawings for purposes of illustration, the invention is embodied in an insertion device for insertion sets such as an infusion set, sensor set, medical device, or the like. Further embodiments of the insertion device may be used to insert other insertion sets or medical devices such as biodegradable implants, capsules, impregnated threads (with medications or the like). Other insertion sets may be directed to a threaded needle insertion set, such as that described in U.S. Pat. No. 5,584,813 issued Dec. 17, 1996 to Livingston et al. entitled "Subcutaneous Injection Set" and U.S. Pat. No. 5,779,665 issued on Jul. 14, 1998 to Mastrototaro et al. entitled "Transdermal Introducer Assembly", which are herein incorporated by reference. In addition, the insertion sets may be coated with medications, or other agents, that inhibit infection and/or promote healing of the insertion site. Preferred embodiments of the insertion device and insertion sets are for transcutaneous placement of the insertion set in subcutaneous tissue. However, in alternative embodiments, the insertion set may be inserted into other subdermal tissues. In addition, still further embodiments may be used to place the sets in other types tissue, such as muscle, lymph, organ tissue or the like, and used in animal tissue. In preferred embodiments of the present invention, the insertion device is loaded with a standard hand-held insertion set, or the like, and then placed against the skin of the user, where the insertion device is activated to transcutaneously place a portion of the insertion set, or the like, subcutaneously in a quick manner that minimizes pain and/or discomfort to the user. However, it will be recognized that further embodiments of the invention may be used to place an entire insertion set, or the like, beneath the skin, rather than just a portion of the insertion set. As discussed, preferred embodiments of the insertion device are designed to accommodate off-the-shelf insertion sets, or the like. But, alternative embodiments may be used with customized insertion sets, or the like that have been altered to fit the insertion device in a particular orientation or configuration to improve safety and/or assure proper placement of the insertion set, or the like. In still other embodiments, the insertion sets, or the like may be angled and the devices are capable of insertion at angles between 0 and 90 degrees relative to the skin surface after insertion of the insertion set.

In preferred embodiments, the insertion set includes at least one piercing member to pierce the skin during insertion. In particular embodiments, the piercing member is a metal needle. In alternative embodiments, the needle may be hollow, solid, half needle (or other fraction), or the like. In further alternative embodiments, the piercing member may be made out of other materials, such as ceramic, plastic, composites, silicon micro-needles, biodegradable, hydrophillic substances, substances that soften and/or change once in contact with the body and/or bodily fluids, or the like. In other alternative embodiments, the insertion set may include more than one piercing member. For example, a single insertion set may include a piercing member for an infusion portion and another piercing member for a separate sensor portion, or the like. Alternatively, the insertion set may include a plurality of small piercing members on a small patch or substrate, such as a series of hollow micro-needles (such as from silicon, plastics, metal or the like) for infusion of a medication or a series of solid micro-needles for sensor applications (such as from silicon, plastics, metal or the like), which micro-needles are used to penetrate the skin.

As shown in the exemplary drawings, an injector (or insertion device) in accordance with a first embodiment of the present invention is referred to generally by the reference numeral 10 is provided for quick and easy transcutaneous placement of a medical needle, particularly such as an insertion needle 12 of the type provided with a subcutaneous insertion set 14 as depicted in FIGS. 4 and 7. The injector 10 includes a trigger-type actuator mechanism for transcutaneous placement of the insertion needle 12 with a controlled speed and force, and with the insertion needle 12 oriented at a desired angular position relative to the skin 16 (FIGS. 1 and 9) of the patient.

The automatic injector 10 of the present invention, as shown in the illustrative drawings, is particularly designed for placement of the insertion needle 12 of a subcutaneous insertion set 14, such as an insertion set of the general type shown and described in U.S. Pat. Nos. 4,755,173; 5,176,662; and 5,257,980, which are incorporated by reference herein. Such insertion sets 14 are used to infuse medical fluids such as selected medications to a patient, with one example being the administration of insulin to a diabetic by operation of a programmable medication infusion pump (not shown) of the type described in U.S. Pat. No. 4,685,903. Alternatively, the injector 10 may be used to transcutaneously place a medical needle associated with other types of insertion sets, such as transcutaneous sensor insertion sets of the general type shown and described in U.S. Pat. Nos. 5,390,671; 5,560,806 and 5,586,553, which are also incorporated by reference herein. Such insertion sets are used, for example, to monitoring patient glucose levels.

As shown best in FIG. 4 with respect to an insertion set 14 for infusing medical fluids to a patient, the insertion needle 12 is connected to a hub 18 at a rear or proximal end thereof, and protrudes through a housing 20 of the insertion set 14, wherein the housing 20 defines an internal chamber (not shown) for receiving medication via infusion tubing 22. An enlarged base, typically in the form of resilient or flexible wings 24, is provided on the housing 20 for stable affixation to the skin 16 of a patient. The insertion needle 12 protrudes downwardly through the housing 20 and the winged base 24 to extend through a soft and flexible cannula 26. The insertion needle 12 is provided for transcutaneous placement of the cannula 26, after which the insertion needle is retracted from the set 14 (FIG. 16) to permit medication delivery through the cannula 26 to the patient.

The injector 10 of the present invention represents a simple device which can be used by the patient to quickly and easily place the subcutaneous insertion set 14 in a proper transcutaneous position and orientation, at a selected medication insertion site. The injector 10 is designed to project the insertion set toward the patient's skin 16 at a controlled force and speed for quickly piercing the skin in a manner insuring proper placement of the insertion needle 12 and cannula 26, while minimizing patient anxiety and/or discomfort. Improper and/or partial placement of the insertion needle 12 is thus avoided.

In general terms, as shown in one preferred form is FIGS. 1-5, the injector 10 comprises a cylindrical forward barrel 28 (or device housing) having a plunger 30 (or carrier body) mounted therein for longitudinal sliding movement within a hollow bore between a forward advanced position (FIG. 5) and a rearward retracted position (FIG. 9). The plunger 30 has a head 32 at a forward end thereof for releasably receiving and retaining the subcutaneous insertion set 14, in a manner to be described in more detail. A rear end of the plunger 30 cooperates with a trigger-type actuator assembly 34 mounted on the rear end of the barrel 28. The trigger actuator assembly 34 (or driver) is adapted to hold the plunger 30 in a retracted position, against the force of a compressed drive spring 36. A trigger button 38 of the actuator assembly 34 is adapted for fingertip depression to release the plunger 30 for spring-loaded travel toward the advanced position, and corresponding transcutaneous placement of the insertion needle 12 through the patient's skin.

FIGS. 2-5 illustrate construction details of the injector barrel 28, wherein the forward or nose end thereof defines a flat and generally planar surface for placement against the skin of a patient (FIG. 1) with a longitudinal axis of the barrel 28 oriented generally perpendicular to the patient's skin 16. The barrel 28 has a size and shape for substantially mated sliding fit reception of the infusion set 14, with the insertion needle 12 and related cannula 26 projecting in a direction for placement on a patient. In this regard, the nose end of the barrel 28 defines an opposed pair of relatively wide and open-ended cut outs 40 for slide-fit reception of the oppositely projecting base wings 24. A narrower slot 42 is also formed in the barrel nose end, at a location for slide-fit reception of the infusion tubing 22 attached to the infusion set 14. Thus, the forward or nose end of the barrel 28 accommodates sliding reception of the subcutaneous insertion set 14 therein for movement along the cut outs 40 and the slot 42 between the advanced position (FIG. 5) disposed substantially at the forwardmost end of the barrel 28, and the retracted position (FIG. 9) with the base wings 24 and infusion tubing 22 positioned substantially at the inboard ends of the cut outs 40 and the associated slot 42.

The plunger 30 includes the bead 32 of generally cylindrical shape for slide-fit reception within the injector barrel 28. A forward end of the head 32 includes a cylindrical counter-bore recess 44 for receiving the hub 18 and housing 20 of the insertion set 14, with the enlarged base wings 24 fitted against a pair of outwardly protruding backstop flanges 46 adapted for slide-fit reception within the cut outs 40 in the barrel nose end. A pair of track arms 48 (FIG. 5) protrude rearwardly from the plunger head 32 and include out-turned latch fingers 50 for guided reception within longitudinally extending track slots 52 formed in the barrel 28 at a location spaced aft from the barrel nose end. These track arms 48 thus cooperate with the barrel track slots 52 to guide the plunger 30 between the advanced position (FIGS. 5 and 7) and the retracted position (FIG. 9).

The plunger 30 also includes a central drive stem 54 (FIG. 5) which protrudes rearwardly from the plunger head 32 within the barrel interior. The rearward end of the drive stem 54 is longitudinally split to define a pair of trigger arms 56 which have out-turned trigger fingers 58 on the rearward ends thereof.

Figure 5:
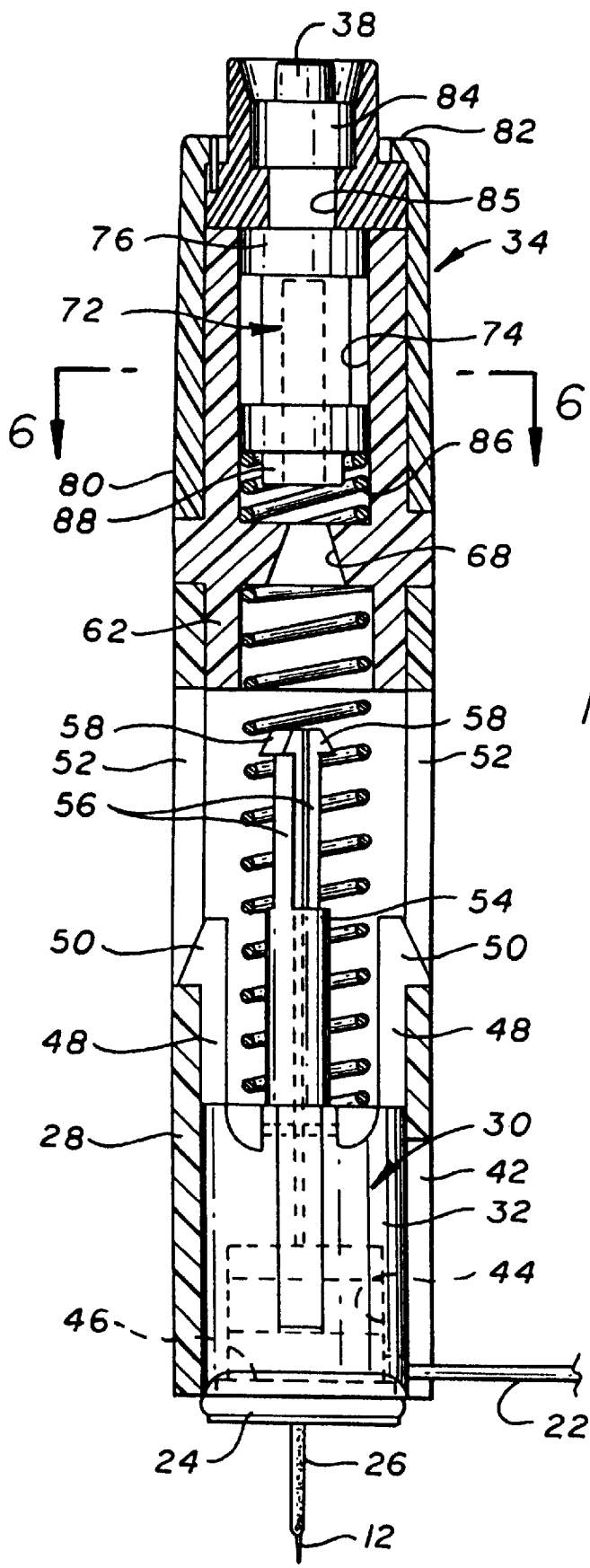
FIG. 5 is a further enlarged longitudinal sectional view taken generally on the line 5-5 of FIG. 4.

The trigger-type actuator assembly 34 is mounted on the rearward end of the injector barrel 28, and generally functions to releasably retain the plunger 30 in a retracted and cocked position, ready for rapid and spring-loaded actuation upon depression of the trigger button 38 to place the insertion set 14 on the patient. More particularly, as shown best in FIGS. 5-9, the trigger assembly 34 comprises a main support cap 60 having a mounting sleeve 62 protruding in a press-fit and preferably adhesively connected manner into the rear or aft end of the injector barrel 28. The drive spring 36 comprises a coil spring positioned about the drive stem 54 on the plunger 30 and reacts between a rearward face 64 of the plunger head 32, and a shoulder 66 on the support cap 60. The drive spring 36 normally biases the plunger 30 toward the advanced position (FIGS. 5 and 7). However, an insertion set 14 seated in the plunger head 32 can be pressed rearwardly against the plunger 30 to move the plunger to the retracted position, as viewed in FIG. 9, with the trigger fingers 58 passed through a conical or tapered latch bore 68 formed in the support cap 60 to engaging a shoulder 70 on an opposite side of the support cap 60. In this regard, the trigger fingers 58 have ramped outboard faces to accommodate movement of the fingers 58 radially toward each other as they pass through the latch bore 68. When the trigger fingers 58 pass entirely through the bore 68, the spring resilience of the trigger arms 56 is sufficient to spread the trigger fingers 58 so that they engage the shoulder 70. In this retracted plunger position, the drive spring 36 is retained in a compressed and cocked condition, with the insertion set 14 including the insertion needle 12 and related cannula 26 withdrawn into the interior of the barrel 28, in spaced relation to the patient's skin 16.

The trigger actuator assembly 34 additionally includes an actuator pin 72 mounted within a noncircular bore 74 (FIGS. 6 and 7) formed in the support cap 60 for longitudinal sliding movement through a short stroke, relative to the plunger 30. In this regard, the actuator pin 72 includes one or more non-circular lands 76 for slide-fit reception within the bore 74, to prevent actuator pin rotation therein. The actuator pin 72 is held within the bore 74 by a stepped lock ring 78 which is retained against a rearward end of the support cap 60 by a press-fit outer retainer sleeve 80 having an inturned rim 82 at the rearward end thereof. Importantly, as shown best in FIG. 8, an oblong land 84 is formed on the actuator pin 72 for mated slide-fit reception through an oblong recess 85 formed in the lock ring 78. A return spring 86 (FIG. 7) is carried within the support cap bore 74 and reacts between the shoulder 70 and a nose end of the actuator pin 80 for biasing the actuator pin 80 rearwardly within the support cap.

Figure 13:
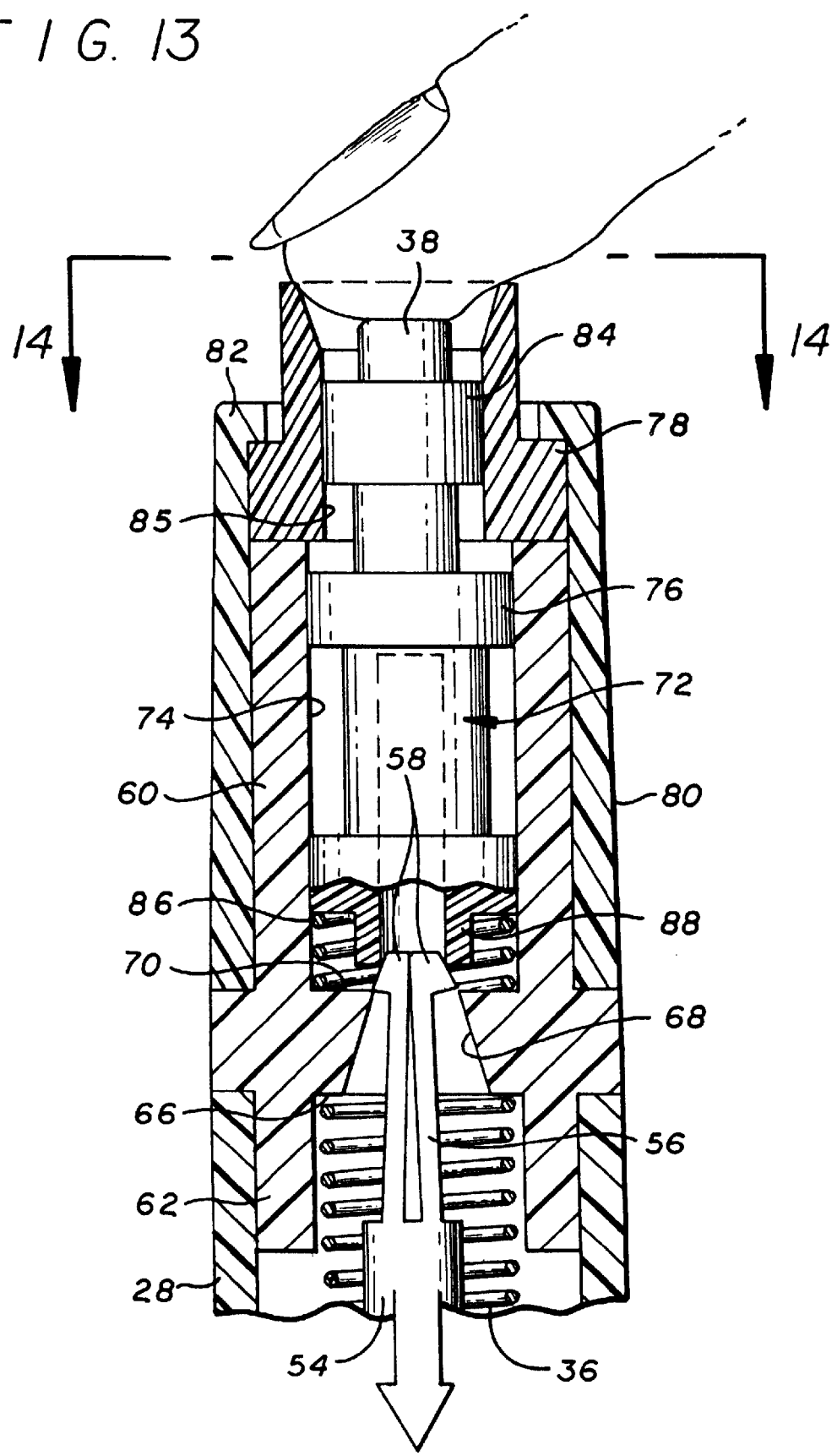
FIG. 13 is an enlarged fragmented longitudinal view similar to a portion of FIG. 11, but depicting actuation of the trigger assembly for releasing the spring-loaded plunger.
Figure 15:
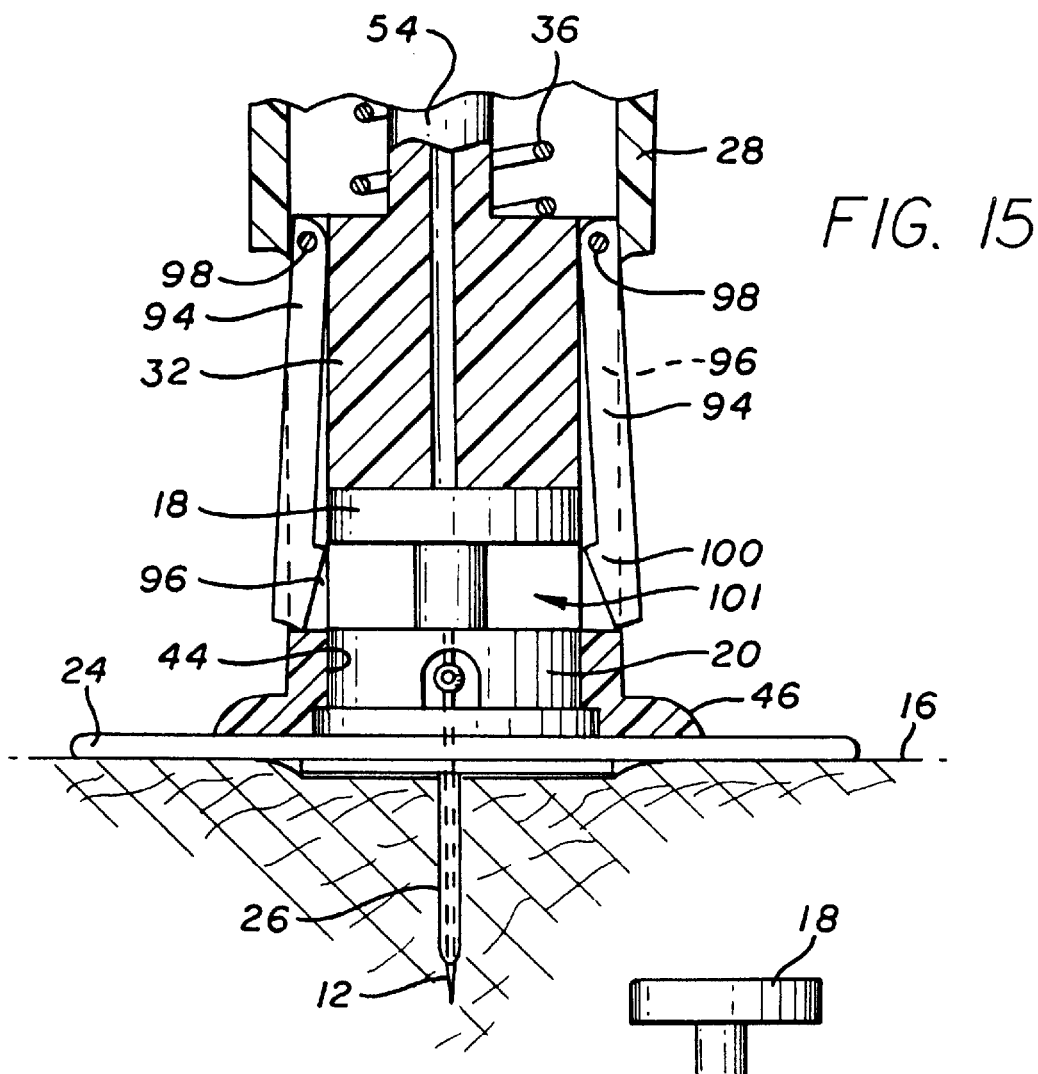
FIG. 15 is a fragmented longitudinal sectional view depicting the spring-loaded plunger in a fully advanced position with the infusion set placed on the patient's skin.

The rearmost end of the actuator pin 72 defines the trigger button 38. As shown in FIGS. 11 and 13, the trigger button 38 can be depressed with a fingertip to move the actuator pin 72 through a short stroke against the return spring 86 in a direction toward the trigger fingers 58 at the rear end of the plunger 30. As shown best in FIG. 13, the actuator pin 72 has a hollowed cylindrical forward tip 88 with a diametric size for engaging and squeezing the trigger fingers 58 together at the rear end of the plunger 30, in a manner enabling those trigger fingers 58 to pass back through the tapered conical latch bore 68. As soon as the trigger fingers 58 thus release from engagement with the shoulder 70 on the support cap 60, the drive spring 36 translates the plunger 30 with the insertion set 14 thereon with a rapid and controlled force and speed toward the advanced position, resulting in transcutaneous placement of the needle 12 and cannula 26, as viewed in FIG. 15. Importantly, the spring rate characteristics of the drive spring 36 and the distance of plunger stroke are chosen for a substantially optimized and proper transcutaneous placement of the needle 12 and cannula 26, all in a manner which minimizes patient discomfort during the needle placement procedure. Moreover, by forming the nose end of the injector barrel 28 with a squared-off shape as shown, the injector 10 can be easily oriented substantially perpendicular to the skin 16 for proper placement of the insertion set.

Depression of the actuator pin 72 by means of the trigger button 38 requires the lock ring 78 to be rotatably oriented in a position aligning the oblong recess 85 therein with the oblong land 84 on the actuator pin. Accordingly, when these oblong structures are rotationally aligned (FIGS. 13-14), the injector 10 is armed for trigger button depression and corresponding release of the retracted and cocked plunger. However, the lock ring 78 can be rotated relative to the actuator pin 72 to misalign these oblong structures, as shown in FIGS. 9-12, whereupon the actuator pin 72 is locked in a rearward position against depression and actuation. A set pin 90 on the lock ring 78 may be provided and received within an accurate notch 92 formed in the retainer sleeve flange rim 82, to permit lock ring rotation back-and-forth through a part circle increment, on the order of about 90 degrees. Appropriate indicia may be applied to the retainer sleeve rim 82, such as the letter "L" for "locked" and the letter "A" for "armed", as viewed in FIGS. 12 and 14, to provide a visual indication of the setting of the trigger assembly 34.

In accordance with one aspect of the invention, the plunger head 32 additionally includes a safety lock mechanism in the form of a pair of safety lock arms 94 pivotally carried in narrow slots 96 formed in the plunger head 32. These safety lock arms 94 have rearward ends connected to the head 30 by pivot pins 98, and forward ends defining contoured lock fingers 100 which protrude into the plunger head recess 44. As shown in FIG. 7, the safety lock arms 94 and their associated lock fingers 100 have a size and shape so that the fingers 100 can engage and retain the hub 18 of the insertion set 14, for example, by fitting into a recess 101 defined between the hub 18 and housing 20 of the insertion set. Importantly, the locations of the lock arm pivot points are chosen to insure that the lock arms 94 engage and retain the insertion set 14 whenever the plunger 30 is moved from the advanced position (FIG. 7) toward and to the retracted position (FIG. 9). When the plunger 30 reaches the fully advanced position, the safety lock arms 94 including their respective pivot pins 98 are disposed within the wide cut outs 40 and are therefore free to swing outwardly, relative to the insertion set 14, to accommodate separation of the insertion set from the injector 10 with a substantially minimum separation force. This configuration has been found to be highly effective as a safeguard to prevent the insertion set 14 from being thrown as a projectile from the injector 10, in the event that the trigger assembly 34 is activated without prior placement of the injector 10 firmly against the patient's skin 16. In use, the subcutaneous insertion set 14 can be placed quickly and easily into the open nose end of the injector barrel 28, within the recess 44 formed in the plunger head 32. Such assembly of the insertion set 14 with the injector 10 requires simple alignment of the base wings 24 and infusion tubing 22 with the appropriate cut outs and slots 40, 42 formed in the nose end of the barrel 28. The insertion set 14 and plunger 30 can then be manually retracted rearwardly, against the drive spring 36, to the retracted position with the plunger 30 cocked and latched as viewed in FIGS. 9 and 11. The injector 10 can then be placed firmly against the patient's skin 16, with the insertion set 14 supported in the proper orientation and at a predetermined distance from the skin 16. Simple depression of the trigger button 38 releases the cocked plunger 30 for spring-loaded travel rapidly albeit with a controlled speed and force of insertion, to ensure penetration of the patient's skin with minimal discomfort, and in a manner which properly places the insertion needle and cannula. The safety lock arms 94 prevent accidental projection of the insertion set 14 through free space, in the event that the trigger button 38 is prematurely depressed. When the insertion set 14 is properly placed, however, the safety lock arms 94 release from the insertion set with minimal force, for easy separation of the injector 10 from the insertion set 14.

Figure 48B:
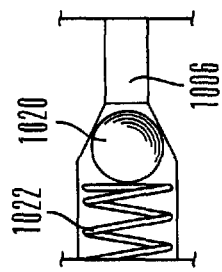
FIGS. 48a-48d are cross-sectional views of a force changing mechanism for use with embodiments of the present invention.
Figure 48D:
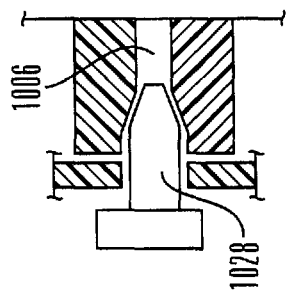
Figure 48A:
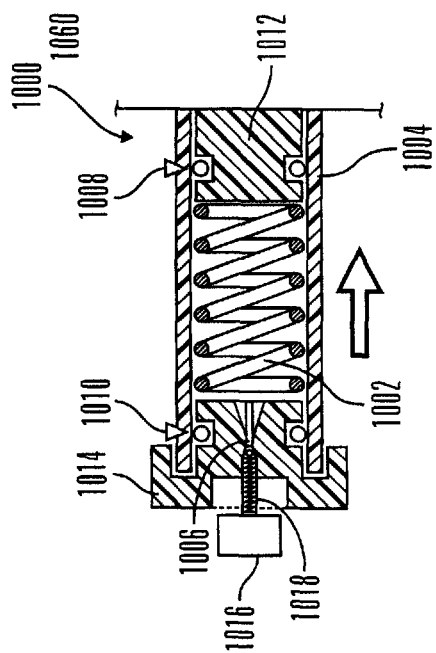
Figure 48C:
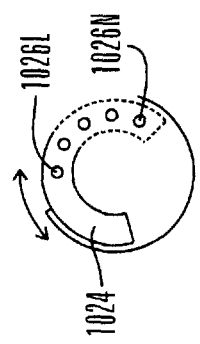

In preferred embodiments, the controlled speed and force of the insertion device is obtained by selecting a spring constant of a spring to propel and insert the insertion set at the proper speed and force to ensure penetration with minimal discomfort. In alternative embodiments, as shown in FIGS. 48a-48d, there is the need to vary the speed and force, from one insertion cycle to the next, to accommodate different insertion sets (such as finer needles, sensor sets fragility or the like) and insertion site conditions (such as overweight, underweight, children or the like). As shown in FIG. 48a, a force changing mechanism 1000 having a spring 1002 enclosed in a sealed compartment 1004 is used with a set (or adjustable) orifice 1006 to allow equalization of internal and ambient pressures during the insertion stroke of the insertion device. The sealed compartment 1004 includes sealing O-rings 1008 and 1010 to seal the sealed compartment 1004. The O-ring 1008 seals the insertion set carrier body 1012, and the O-ring 1010 seals the actuator housing 1014 (which contains the orifice 1006) of the force generating mechanism 1000. The force changing mechanism 1000 may be activated by, for example, a trigger 1016 that is biased by a spring 1018 to close off the orifice 1006 until depressed. The limiting flow through the office 1006 acts as a dampening force, counteracting the spring force from the spring 1002, thereby allowing control of insertion speed and force. The orifice size can be adjustably attained through a number of approaches, such as bearing 1020 and spring 1022 that blocks the orifice 1006 and resists air flow based on the tension of the spring 1022 on the bearing 1020 (see FIG. 48b); while presenting a lower resistance during retraction as the air contained in the sealed compartment 1004 is compressed, forcing bearing 1020 against spring 1022 to unseat the bearing 1022 from the orifice 1006 to present the maximum orifice size for escaping air during compression of spring 1002. This structure minimizes the force needed to compress spring 1022 by allowing air in the sealed compartment 1004 to escape freely and quickly through the orifice 1006; rather than be compressed within the sealed compartment 1004 because the orifice 1006 is restricted by bearing 1002. In another alternative, as shown in FIG. 48c, a disk 1024 has a plurality of various sized holes 1026(1) to 1026(n). The disk 1024 is rotateable over the orifice 1006 to sequentially obstruct, completely obstruct or partially obstruct the orifice 1006 flow path and changes the effective size of the orifice 1006 by blocking the orifice 1006 with the various sized holes 1026(1) through 1026(n). In another embodiment, as shown in FIG. 48d, a tapered valve plug 1028 is threaded into position relative to the orifice 1006 to change the effective size of the orifice 1006. Other orifice 1006 size changing methods may be used. In addition, other methods of controlling the insertion speed and force may be used, such as controlled friction, change in spring tension, hydraulics, pneumatics or the like may be used.

Figure 16:
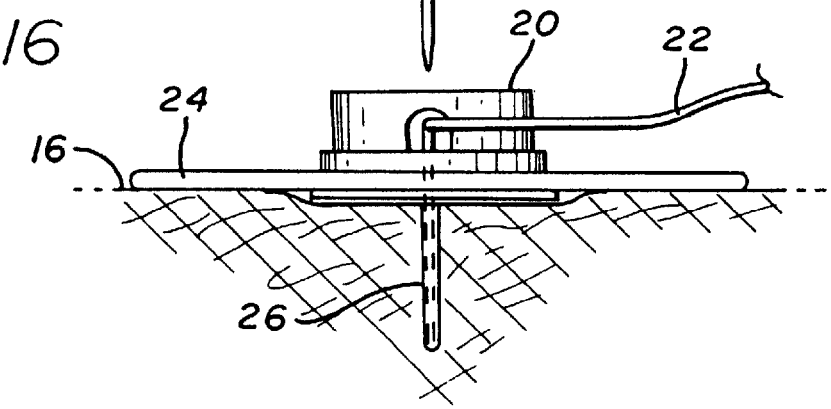
FIG. 16 is an exploded perspective view illustrating separation of the insertion needle from the cannula of the subcutaneous insertion set.

Following separation of the injector 10 from the placed insertion set 14, the insertion needle 12 can be withdrawn quickly and easily from the cannula as viewed in FIG. 16. Thereafter, the insertion set 14 can be used in a normal manner to deliver a selected medication through the infusion tubing 22 and cannula 26 to the patient.

An alternative preferred form of the invention is shown in FIGS. 17-29, wherein components corresponding in structure and function to those described previously with respect to FIGS. 1-16 are identified by common reference numerals increased by 100. The embodiment of FIGS. 17-29 show a modified injector 110 constructed from a reduced number of parts and including an alternative safety lock mechanism for preventing undesired projection of the insertion set 14 through free space in the event of injector operation without placing the nose end thereof firmly against the skin 16 of a patient. However, the alternative safety lock mechanism again permits quick and easy separation of the injector 110 from the insertion set 14, with minimal separation force. Once again, although an insertion set for infusing medical fluids to a patient will be shown and described, it will be understood that alternative insertion sets such as transcutaneous sensor insertion sets and the like as previously referenced herein may be used with the injector 110.

In general, the modified injector 110 comprises a plunger 130 and a trigger-type actuator 134 assembled with a generally cylindrical hollow barrel 128. The plunger 130 has a generally cylindrical plunger head 132 which defines a counterbore recess 144 for receiving and retaining the hub 18 of the infusion set 14. As shown best in FIGS. 27-29, a radially inwardly projecting rim 202 is formed on the plunger head 132 generally at a leading or nose end of the recess 144, wherein this rim 202 has a noncircular and preferably oval or elliptical shape (FIG. 28) to accommodate reception of the hub 18 into the recess 144 provided that the hub 18 is oriented angularly relative to a central longitudinal axis of the plunger 130 and barrel 128. Similar angular orientation of these components accommodates quick and easy separation thereof. However, when the insertion set 14 is oriented with the medical needle 12 aligned coaxially with the barrel center axis, a portion of the rim 202 projects into the insertion set recess 101 to prevent release of the insertion set 14 from the injector 110.

More specifically, with reference to FIGS. 17-20, the barrel 128 again has a forward or nose end defining a flat and generally planar surface for firm placement against the skin of a patient. The nose end of the barrel 128 has a pair of relatively wide and generally opposed cut outs 140 formed therein for slide-fit reception of the base wings 24 of the insertion set 14, in combination with a narrower slot 142 for slide-fit reception of the infusion tubing 22. This slot 142 may be formed in one or both sides of the barrel nose end.

The plunger 130 is slidably fitted into the barrel 128 for movement between an advanced position shown in FIGS. 17, 18, 20 and 21, and a retracted position shown in FIG. 23. The plunger 130 includes the modified plunger head 132 of generally cylindrical shape, formed preferably to include a shallow notch or groove 133 in one side thereof for slide-fit reception of the infusion tubing 22 on the insertion set 14. In this regard, the plunger head groove 133 is formed in a position aligned with the narrow slot 142 in the nose end of the barrel.

The plunger head 132 is formed integrally with a drive stem 154 which projects rearwardly within the barrel interior. As shown best in FIG. 22, the drive stem 154 is flanked by and formed integrally with a pair of rearwardly projecting track arms 148 which have latch fingers 150 formed at the rear ends thereof. As shown in FIGS. 21 and 23, these latch fingers 150 are received slidably within longitudinally extending track slots 152 formed in the barrel 128, and function to guide the plunger 130 between the advanced and retracted positions. Cushioning material (not shown) may be included at the leading ends of the track slots 152 to form a combined stop upon spring driver advancing motion of the plunger 130, as will be described.

The plunger 130 additionally includes a pair of trigger arms 156 which project generally rearwardly from a rear end of the drive stem 154 and have out-turned trigger fingers 158 at the rear ends thereof (FIG. 22). These trigger fingers 158 are adapted and sized for partial radial compression toward each other as they ride within the barrel base when the plunger 130 is displaced from the advanced position (FIG. 21) to the retracted position (FIG. 23). As the retracted position is reached, the trigger fingers 158 are spring-loaded by the resiliency of the trigger arms 156 to move outwardly for partial reception into relatively short trigger slots 159 formed in the barrel 128. In this position, as shown in FIG. 23, the triggers fingers 158 retain the plunger 130 in the retracted position.

A drive spring 136 is mounted within the barrel 128 to react between the trigger-type actuator 134 and the plunger 130, in the same manner as previously described with respect to FIGS. 1-16. In this regard, the trigger actuator 134 comprises a generally cylindrical actuator sleeve 188 mounted slidably within the barrel 128 at the rear or upper end thereof. This actuator sleeve 188 has a tapered or ramped leading edge face 188' (FIGS. 22, 23 and 25) for engaging matingly shaped ramped outer faces of the trigger fingers 158, to radially compress the trigger arms 156 and release the plunger 130 for spring-loaded travel from the retracted and cocked position to the advanced position. A trigger button 138 is formed integrally with the actuator sleeve 188 and is exposed for fingertip depression at the rear or top of the barrel 128 to move the actuator sleeve 188 into releasing engagement with the trigger fingers 158.

As shown best in FIGS. 22 and 24-26, the triggers button 138 extends through an opening formed in the rear of the barrel 128, generally within a lock sleeve 178 formed integrally with the barrel 128. The lock sleeve 178 defines an oppositely formed pair of guide slots 192 for aligned reception of a pair of outwardly radiating lock tabs 184 formed on the trigger button 138. When the tabs 184 and rotationally aligned with the guide slots 192, the trigger button 138 can be depressed to actuate the spring-locked plunger, as described. However, the lock tabs 184 have sufficient length to permit fingertip rotation of the actuator 134 to re-position the tabs 184 within shallow lock grooves 193 formed adjacent the guide slots 192. When the tabs 184 are seated in the lock grooves 193, the lock sleeve 178 blocks depression of the triggers button 138 and thereby locks the injector 110 against actuation. Return rotation of the actuation 134 to re-align the tabs 184 with the guide slots 192 is required before the injector can be activated.

In accordance with one aspect of the invention, the plunger head 132 includes the safety lock mechanism in the form of the noncircular rim 202 at the leading end of the recess 144 in the plunger head. As shown in FIGS. 27 and 28, the rim 202 has a generally elliptical shape defining a major axis that is greater than the diameter of the hub 18 on the insertion set 14, and a minor axis that is less than the hub diameter. With this geometry, and by providing sufficient axial depth to the plunger head recess 144, the hub 18 can be fitted into the plunger head by angularly orienting the components to permit slide-fit of the hub 18 through the major axis portion of the rim 202. Subsequent re-orientation of the components to align the medical needle 12 generally coaxially with plunger head 32 enables the minor axis portion of the rim 202 to project into the insertion set recess 101, thereby locking the components together. Thereafter, when the insertion set 14 is placed on the patient (FIG. 29), the components are easily separated by lifting the injector 110 off the insertion set 14 at the same angle to allow the hub 18 to press freely through the major axis center of the rim 202. Importantly, such engagement and disengagement of the components occurs with essentially no resistance force to separation. The infusion set 14 can be oriented angularly relative to the plunger 130 only when the plunger is in the advanced position, with the adjacent barrel 128 precluding such angular orientation when the plunger 130 is moved rearwardly from the restricted position.

In an alternative mode of operation, subsequent to actuation of the injector 110 to place the insertion set 14 of the patient, the injector 110 can be simply withdrawn or retracted in a direction away from the patient's skin 16, in which case the rim 202 at the nose end of the plunger head 132 will engage the needle hub 18 and thereby gently withdraw the medical needle 12 from the insertion set 14. In this manner, the needle 12 is retracted from the cannula 26 which remains at the desired transcutaneous insertion site.

Figure 30:
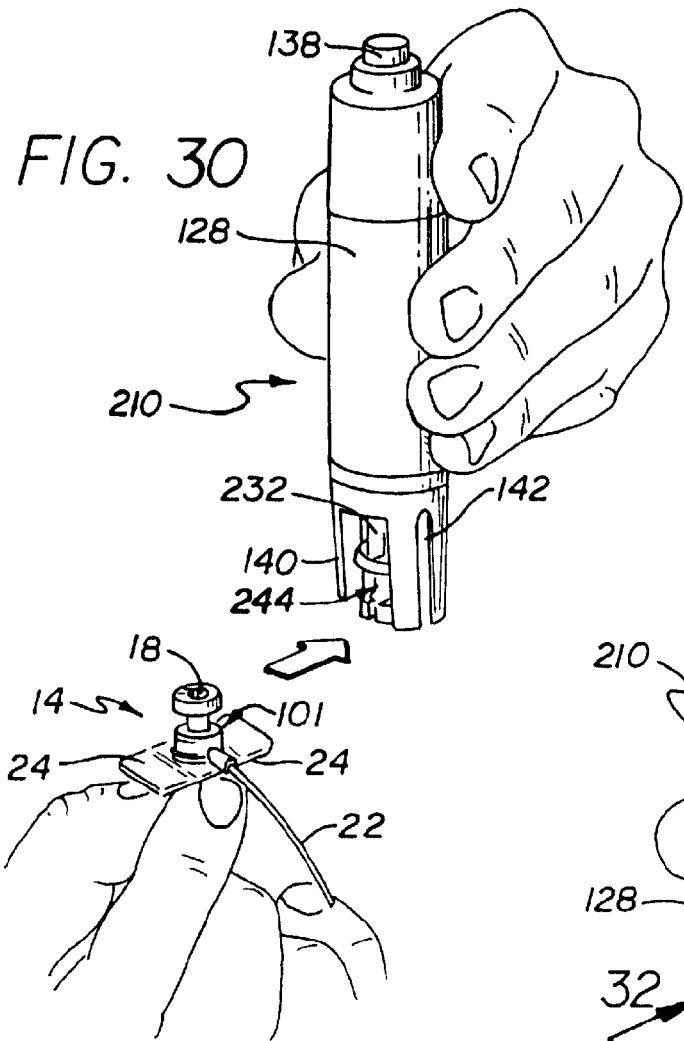
FIG. 30 is an exploded prospective view generally similar to FIG. 17, but depicting a further alternative preferred form of the invention, and showing assembly of an insertion set with the illustrative injector.
Figure 31:
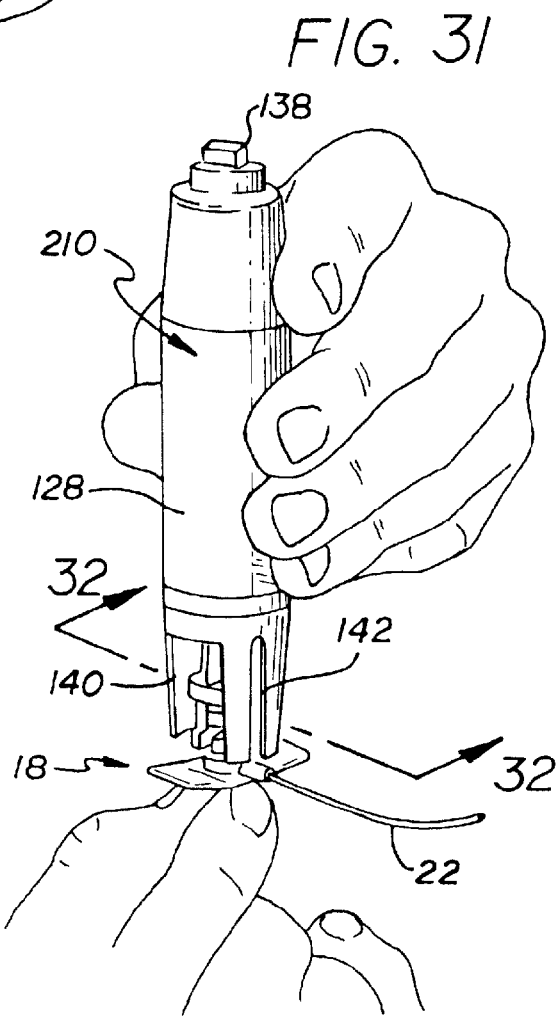
FIG. 31 is a perspective view similar to FIG. 32, depicting further assembly of the insertion set with the injector.
Figure 32:
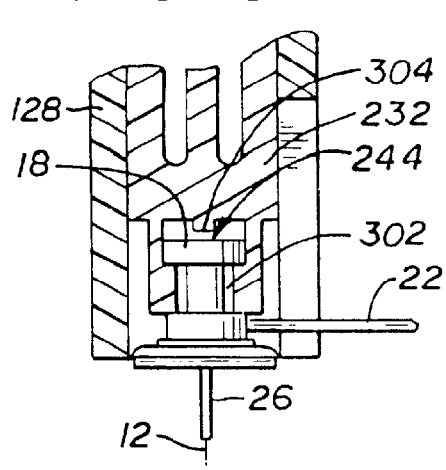
FIG. 32 is an enlarged fragmented vertical sectional view taken generally on the line 32-32 of FIG. 31.
Figure 33:
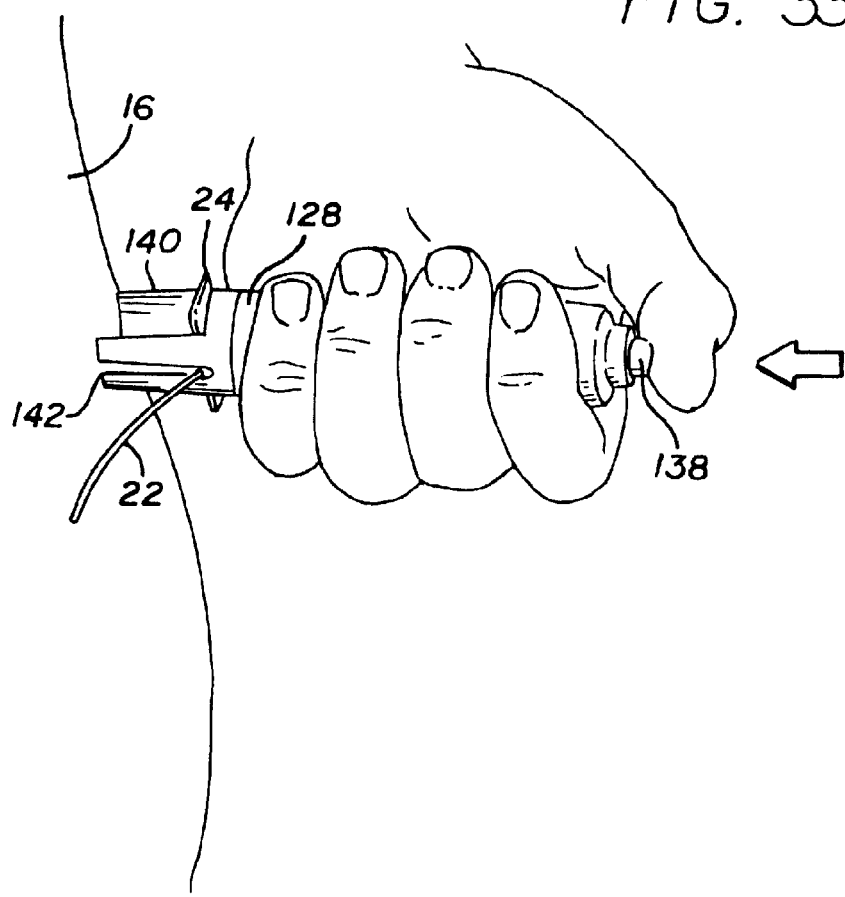
FIG. 33 is a perspective view showing use of the injector of FIGS. 30-32 for transcutaneous placement of the insertion set.
Figure 34:
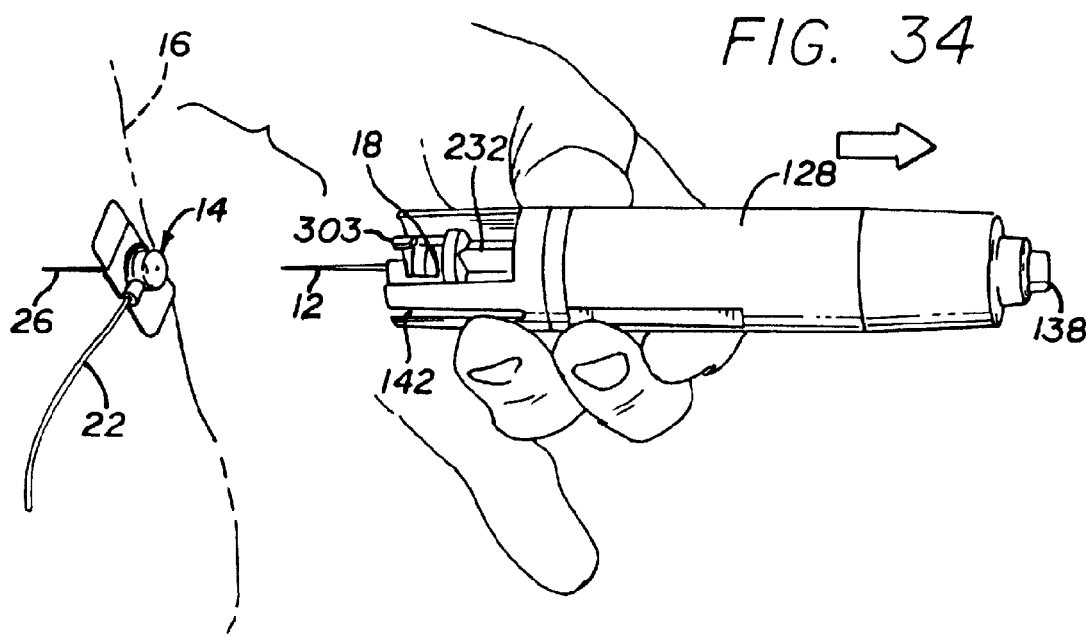
FIG. 34 is an exploded perspective view similar to FIG. 33, and showing use of the injector to separate a medical needle from the installed insertion set.
Figure 38:
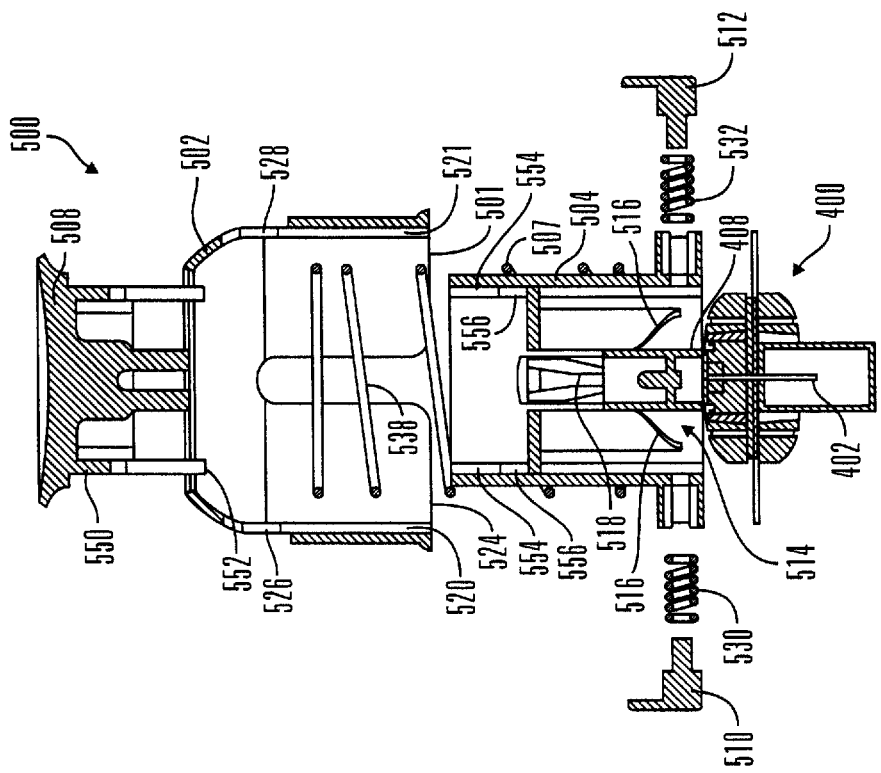
FIG. 38 is an exploded cross-sectional view of the insertion device and the one type of insertion set as shown along the line 38-38 in FIG. 37.
Figure 37:
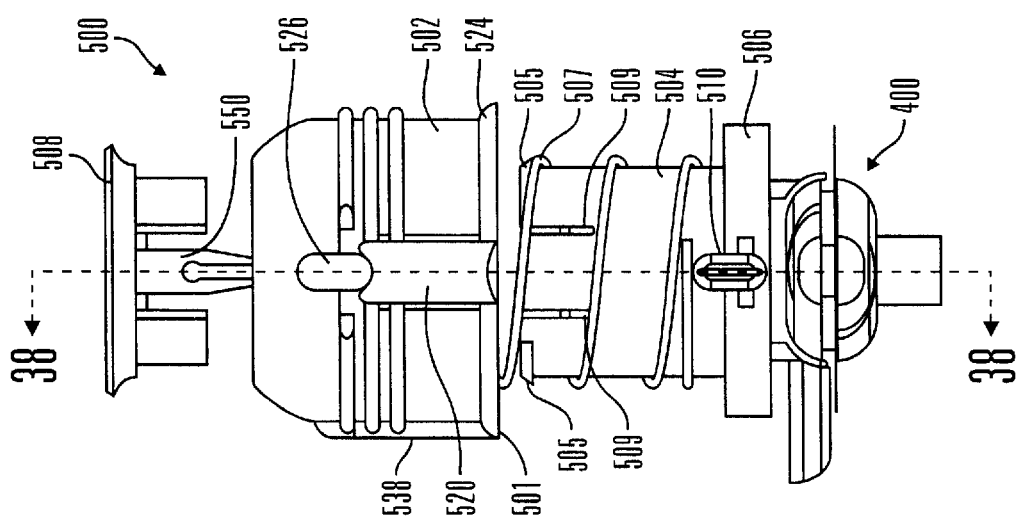
FIG. 37 is a side plan view of the insertion device and insertion set shown in FIG. 35.
Figure 39:
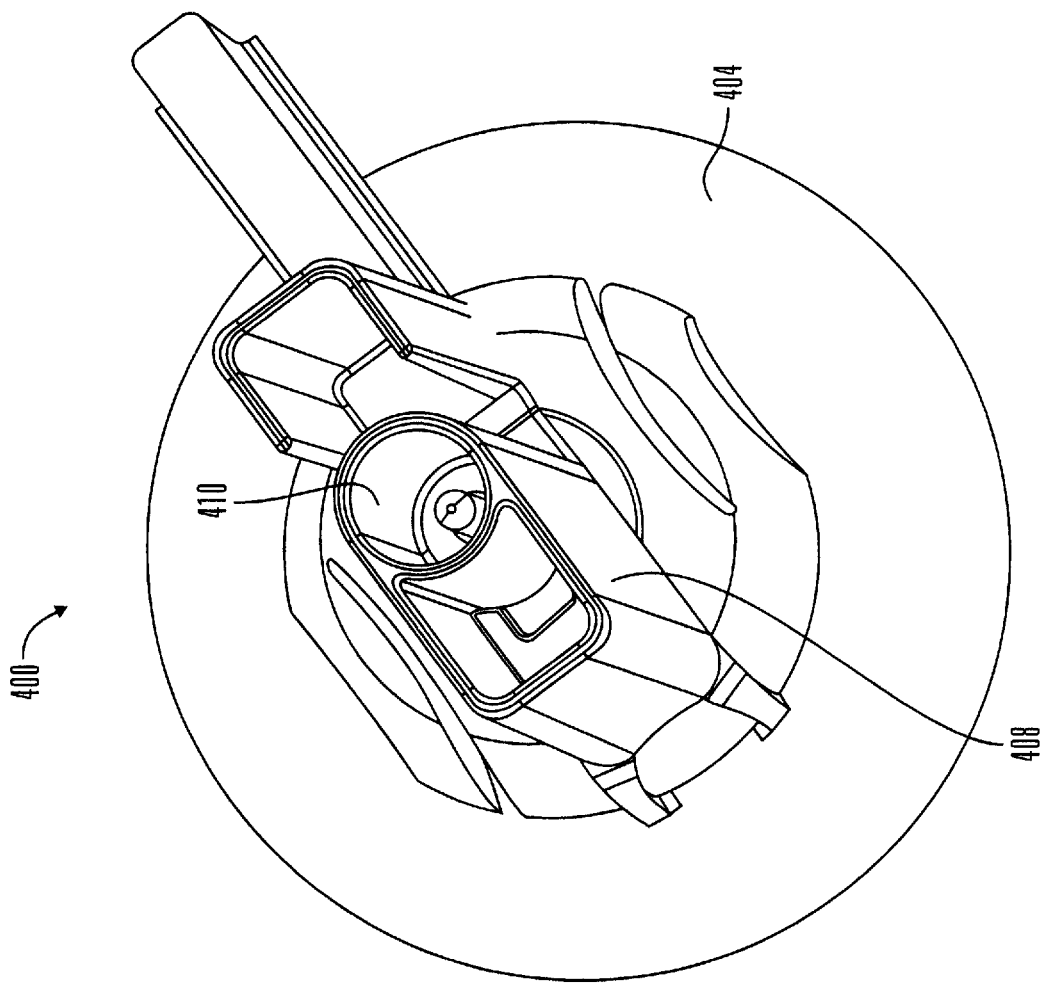
FIG. 39 is a top perspective view of one type of insertion set for use with the insertion device shown in FIG. 35.

A further alternative preferred form of the invention is shown in FIGS. 30-34, wherein a further modified injector 210 is constructed and operated generally as shown and described in FIGS. 17-29, but wherein an alternative configuration for a plunger head 232 is provided. FIGS. 30-32 show the injector 210 with the plunger head 232 in the advanced position within the front or nose end of the barrel 128 which includes the wide cut outs 140 and the narrow slot 142 for respective slide-fit reception of the base wings 24 and the tubing 22 of the insertion set 14. As shown, the modified plunger head 232 has a laterally open recess 244 formed therein of undercut geometry and laterally exposed through the cut outs 140 when the plunger is in the advanced position. The insertion set 14 can be slide-fit assembled with the plunger head 232, by fitting the hub 18 into the wider upper region of the recess 144, with an inturned rim 302 at the leading end of the plunger head fitting into the insertion set recess 101. A laterally open gap 303 (FIG. 34) in the rim 302 permits slide-fit reception of the hub 18 into the recess 244, and a short carrier post 304 (FIG. 32) may be provided at the base of the recess 244 to seat within a shallow detent in the top of the hub.

With the insertion set 14 assembled with the plunger head 232, as viewed in FIG. 32, the plunger can be retracted and cocked as previously shown and described with respect to FIGS. 17-29. The cut outs 140 and slot 142 accommodate sliding movement of the insertion set 14 with the plunger 232 during such retraction. Thereafter, the front or nose end of the injector 210 can be placed firmly against the patient's skin (FIG. 33) and the trigger button 138 depressed to release the plunger so that the medical needle 12 is transcutaneously placed with the controlled drive force and speed. During forward drive motion of the plunger, the forward rim 302 on the plunger head 232 prevents projectile release of the insertion set. After placement of the insertion set on the patient, the injector 210 can be laterally displaced relative to the insertion set for quick and easy separation therefrom. Alternately, as viewed in FIG. 34, the injector 210 can be withdrawn or retracted from the insertion set 14 to slidably withdraw the medical needle 12 while leaving the insertion set in place on the patient.

FIGS. 35-40g illustrate an insertion device 500 in accordance with a second embodiment of the present invention. The insertion device 500 includes a barrel 502 (or device housing) having a surface seat 501 and an assembly port 503, a carrier body 504 (or plunger or the like) having an assembly rim 505 and a seating flange 506, a drive spring 507 (or driver), a release button 508, and dual spring triggers 510 and 512. As shown in FIG. 35, the barrel 502 performs as a housing to hold the carrier body 504. The carrier body 504 is connected to the barrel 502 by the carrier body being inserted through an opening in the surface seat 501 of the barrel 502, and then passing the assembly rim 505 of the carrier body 504 through the assembly port 503 of the barrel 502. The section of the carrier body 504 with the assembly rim 505 compresses slightly, as it passes through the assembly port 503, due to the presence of compression slots 509, and then essentially restores to its original shape to prevent the carrier body 504 from sliding out of the barrel 502, since the assembly rim 505 of the carrier body engages with the assembly port 503 of the barrel 502.

The carrier body 504 is driven to an advanced position from a retracted position by the drive spring 507 and held in the retracted position (or released to move to the advanced position) by the trigger buttons 510 and 512. This embodiment of the insertion device 500 is primarily adapted for insertion of insertion sets 400 (as exemplary shown in FIG. 39 as an infusion set), or the like, that are inserted with the piercing member 402 (or needle) at 90 degrees (or perpendicular) to the skin surface after insertion. In preferred embodiments, the carrier body 504 is permanently coupled to the barrel 502 and new insertion sets 400 are attached to the carrier body 504 for each new insertion. However, in alternative embodiments, the carrier body 504 may be a disposable that is replaced after each insertion so that, for instance, a carrier body 504 may be shipped with a pre-installed insertion set 400 and then loaded into the barrel 502 of the insertion device 500.

The insertion device 500 features a low profile compact package that tends to minimize the effects of hand movement during insertion of the insertion set 400. In this embodiment, the release button 508 is depressed to release the insertion set 400, or the like, from the carrier body 504 of the insertion device 500; rather than engaging or disengaging the insertion set 14 using a lateral slot as shown in FIGS. 31-34 above. The release button 508 can be used before or after insertion of the insertion set 400, or the like. To facilitate insertion of an insertion set 400, or the like, the insertion device 500 utilizes dual trigger buttons 510 and 512, which provide an extra margin of safety and substantially prevents accidental activation of the insertion device 500 upon contact with the skin surface. This obviates the need for a lock and unlock position on the activation buttons (or triggers) of the earlier insertion devices shown in FIGS. 1-34. The insertion device 500 also includes another rim on the carrier body 504 that forms the seating flange 506 to hold a rim 404 (or wing) of the insertion set 400, or the like, that carries an adhesive 406 for adhering the insertion set 400 to the surface of the skin. Upon activation of the insertion device 500 to move the carrier body to the advanced position, the seating flange 506 presses the adhesive 406 and rim 404 of the insertion set 400 firmly against the skin surface to provide positive seating and attachment of the insertion set 400 to the skin. This may make it unnecessary to require placement of an additional adhesive patch prior to or after inserting an insertion set 400 to secure the insertion set 400 at the insertion site. The insertion device 500 further includes an automatic release of the piercing member (or needle) hub 408 and piercing member 402 (or needle) from the insertion set 400, or the like, after the insertion set 400, or the like, has been inserted. This permits the insertion set 400 to be left on the skin surface without the piercing member hub 408 and piercing member 402 (or needle) remaining by simply removing the insertion device 500 from the skin surface. This automatic release feature also minimizes potential patient contact with the piercing member 402 (or needle) of the insertion set 400, or the like.

In preferred embodiments, the insertion set 400, or the like, is adapted to tightly fit within a cavity 514 (or receiving structure) of the carrier body 504. The cavity 514 of the carrier body 504 includes guides 516 to orient the insertion set in a particular orientation and an expansion member 518 in the center bottom interior of the cavity 514 of the carrier body 504 to engage with the piercing member hub 408 (or needle hub) of the insertion set 400, or the like. The piercing member hub 408 of the insertion set 400, or the like, includes a center section 410 that engages with the expansion member 518 with a slight interference fit. The interference fit expands the center section 410 of the piercing member hub 408 slightly to expand and press the piercing member hub 408 against the sides of the cavity 514 of the carrier body 504 to firmly secure the insertion set 400, or the like, within the cavity 514 of the carrier body 504. The tight fit of the insertion set 400, or the like, in the carrier body 504 substantially prevents the insertion set 400, or the like, from being dislodged when the insertion device 500 is activated to improve insertion of the insertion set 400, or the like, on the skin. However, the tight fit also prevents the insertion set 400, or the like, from being ejected if the insertion device 500 is inadvertently activated when it is not pressed against the skin surface. In preferred embodiments, the insertion device 500 is configured to have guides 516 and an expansion member 518 to work with existing insertion sets 400, or the like. However, in alternative embodiments, the insertion set 400, or the like, may be modified to have a piercing member base, housing or the like that includes slots (not shown) for receiving guides and expanding members of the insertion device 500 to improve the connection between the insertion device 500 and the insertion set 400, or the like. In further alternative embodiments, the guides and expansion members may be formed on the insertion set 400, or the like, and the corresponding guide slots and expanding sections may be formed on the insertion device 500.

The illustrated embodiment employs a dual trigger activation structure to minimize the ability of the insertion device 500 to be unintentionally activated. As illustrated, the barrel 502 of the insertion device 500 includes two outwardly extending guide channels 520 and 522 on the side of the barrel 502. The guide channels 520 and 522 extend from the base 524 of the barrel 502 up to portal openings 526 and 528 in the side of the barrel 502. The dual trigger buttons 510 and 512 are carried on opposite sides of the seating flange 506 at the end of the carrier body 504. Each trigger button 510 and 512 is biased outward from the side of the seating flange 506 by a trigger spring 530 and 532 between the end of the trigger buttons 510 and 512 and the side of the seating flange 506. When the carrier body 504 of the insertion device 500 is locked in the firing position (or retracted position), the trigger buttons 510 and 512 are pushed out by the trigger springs 530 and 532 to extend out of the portal openings 526 and 528. In this position, the trigger buttons 510 and 512 extend beyond the bottom of the guide channels 520 and 522, which prevents the trigger buttons 510 and 512 from moving down the guide channels 520 and 522. To activate the insertion device 500, the user must depress both trigger buttons 510 and 512 so that the trigger buttons 510 and 512 can then slide along the bottom of the guide channels 520 and 522, which in turn allows the carrier body 504 to move down along the barrel 502 until the insertion set 400, or the like, is inserted. In preferred embodiments, the portal openings 526 and 528 and the end of the guide channels 520 and 522 terminating at the portal openings 526 and 528 are rounded to match the shape of the trigger buttons 510 and 512. This tends to minimize the resisting pressure on the trigger buttons 510 and 512 during depression of the trigger buttons 510 and 512. However, in alternative embodiments other portal opening and guide channel end shapes, such as beveled, squared, polygonal, or the like, may be used.

The end of the carrier body 504 having the assembly rim 505 is connected to a release button 508 that can be depressed or slightly extended relative to the carrier body 504. The release button 508 includes engagement tabs 550 and lock teeth 552 (see FIGS. 35 and 36) that engage with carrier slots 554 and carrier locks 556 (see FIGS. 36 and 38) to lock the release button 508 to the carrier body 504. The lock teeth 552 engage with the carrier locks 556 (see FIGS. 36 and 38) to permit an amount of movement of the lock teeth 552 along the carrier locks 556 to allow the release button 508 to be depressed to release an insertion set from the carrier body 504. The release button 508 is also slightly extended away from the carrier body 504 when an insertion set 400 is placed in the interior cavity 514 of the carrier body 504 to permit seating of the insertion set 400. Engaging the release button 508 with the carrier body substantially prevents the compression slots 509 and assembly rim 505 from compression and inhibits release of the carrier body 504 from the barrel 502 of the insertion device 500.

The release button 508 is depressed to release the insertion set 400, or the like, from the carrier body 504 of the insertion device 500. The release button 508 pushes the insertion set 400, or the like, out of the cavity 514 of the carrier body 504 sufficiently enough to release the insertion set 400, or the like, from the guides 516 and the expanding member 518 in the cavity 514 and leave the inserted insertion set 400, or the like, on the skin. Alternatively, the release button 508 may be activated to release an insertion set 400, or the like, from the carrier body 504 prior to the insertion set 400, or the like, being inserted by the insertion device 500. The release button 508 also includes a ramp portion 534 (or other trigger mechanism) that is adapted to bend or adjust the piercing member hub 408 (or needle hub) of the insertion set 400, or the like, to allow the piercing member hub 408 and piercing member 402 (or needle) to be released and separated from the insertion set 400, or the like, when the insertion set 400, or the like, has been inserted and the insertion device 500 is lifted off the skin. This can be accomplished by separating the elements of the insertion set 400, or the like, so that only the insertion set, or the like, housing and tubing (or wiring or the like) are left in contact with the skin. The ability to remove the piercing member hub 408 and piercing member 402 is preferably facilitated by the adhesive 406 of the insertion set 400, or the like, that attaches to the skin to provide sufficient tension to allow for separation of the piercing member hub 408 and the piercing member 402 from the rest of the insertion set 400, or the like, without dislodging the insertion set 400, or the like. In preferred embodiments, the insertion device 500 is adapted to work with an existing piercing member hub 408 on an insertion set 400, or the like. However, in alternative embodiments, the piercing member hub 408 and the connection between the piercing member hub 408 and the insertion set housing, or the like, is modified to work with the release mechanism of the insertion device 500.

In preferred embodiments, the release button 508 is biased in position by a plastic or metal spring. However, in alternative embodiments, the release button 508 may be manually reset by engaging and disengaging detents or using other elastomeric materials to bias the release button 508 in position relative to the barrel 502 and the carrier body 504. In preferred embodiments, pulling up the release button 508 (or extending it away from the assembly port 503 of the barrel 502) pulls the carrier body 504 to the retracted position in the barrel 502, where it is locked in place by triggers 510 and 512 engaging the portal openings 526 and 528. This procedure separates the piercing member hub 408 and piercing member 402 from the housing of the insertion set 400, or the like. This has the advantage of removing the piercing member 402 and piercing member hub 408 to minimize the opportunity of a user being stuck by the piercing member 402.

Figure 40B:
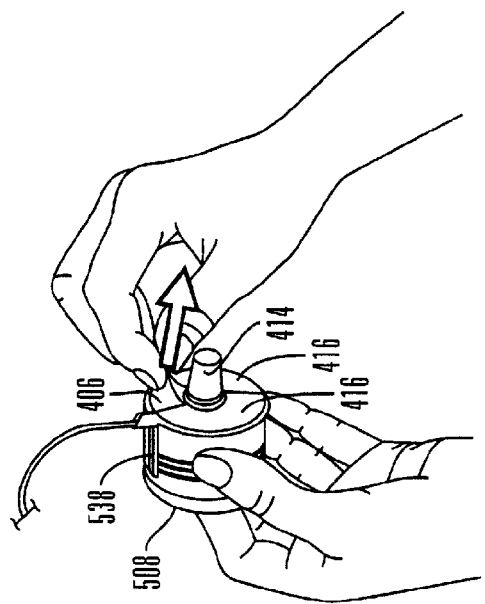
FIGS. 40a-40g illustrate the steps of inserting the one type of insertion set of FIG. 39 with the insertion device of FIG. 35.
Figure 40D:
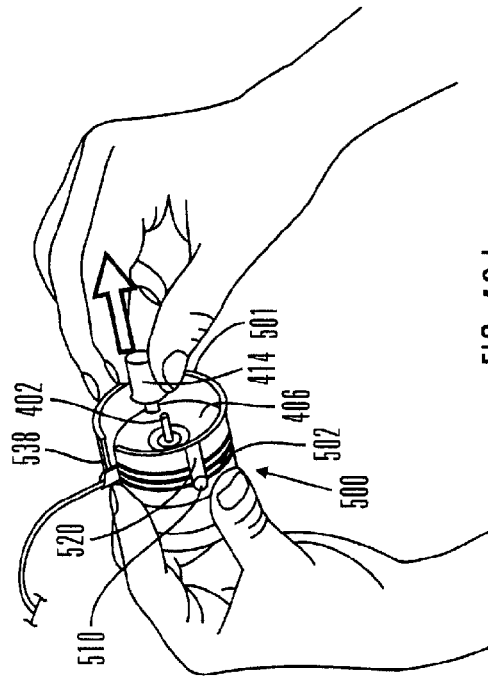
Figure 40A:
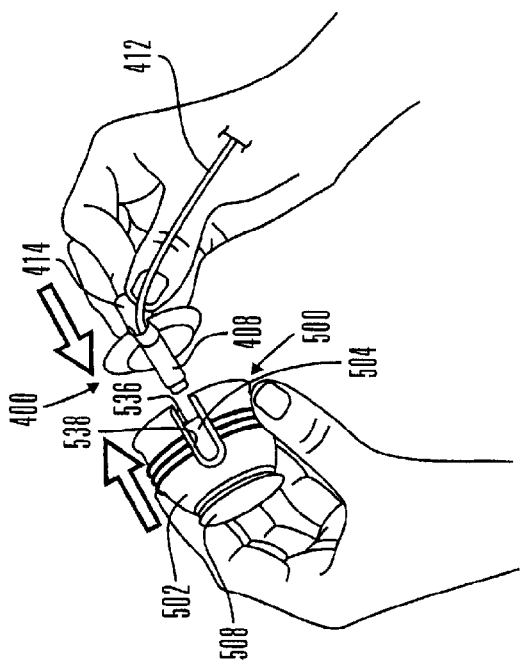
Figure 40C:
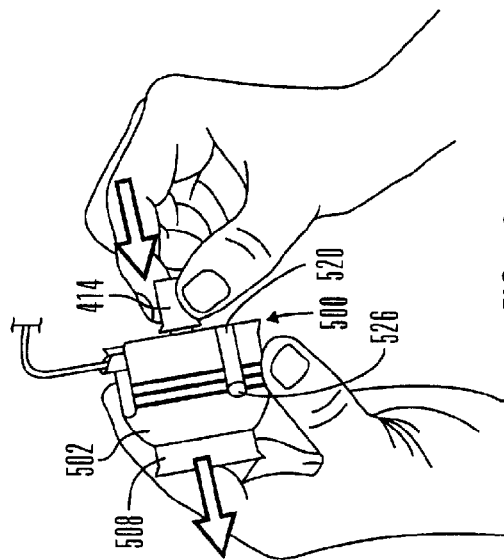
Figure 40F:
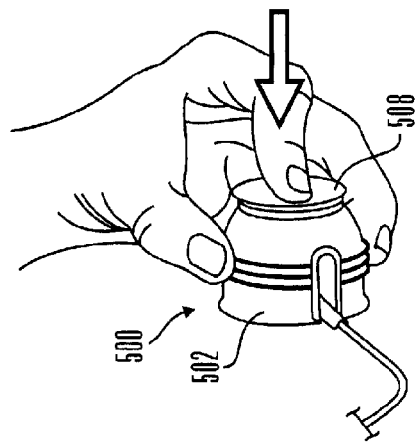
Figure 40G:
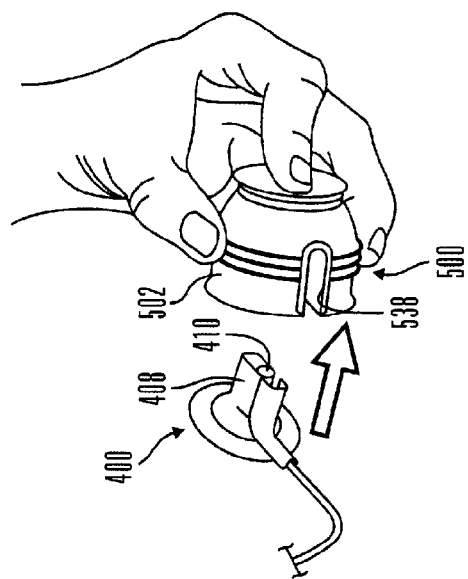
Figure 40E:
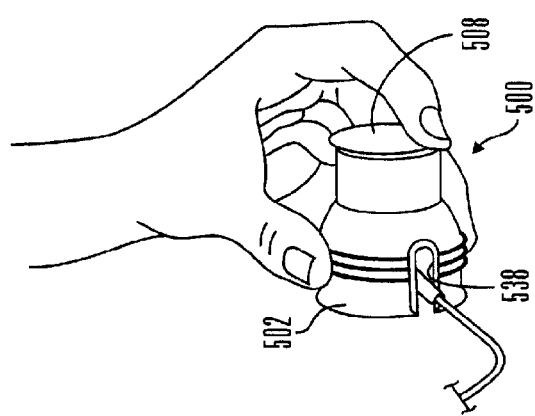
Figure 43:
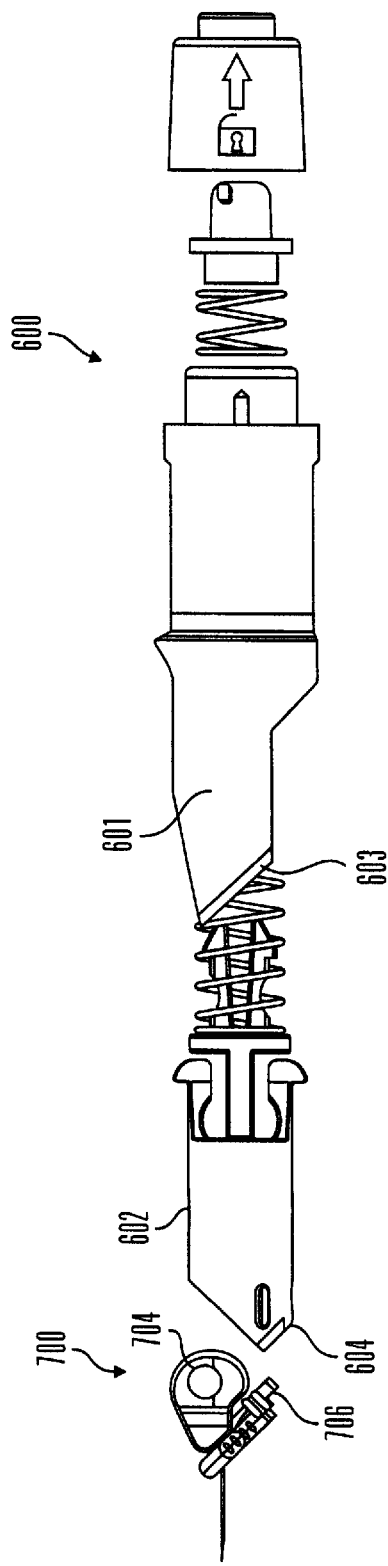
FIG. 43 is an exploded side plan view of the insertion device and the one type of insertion set shown in FIG. 41.
Figure 44:
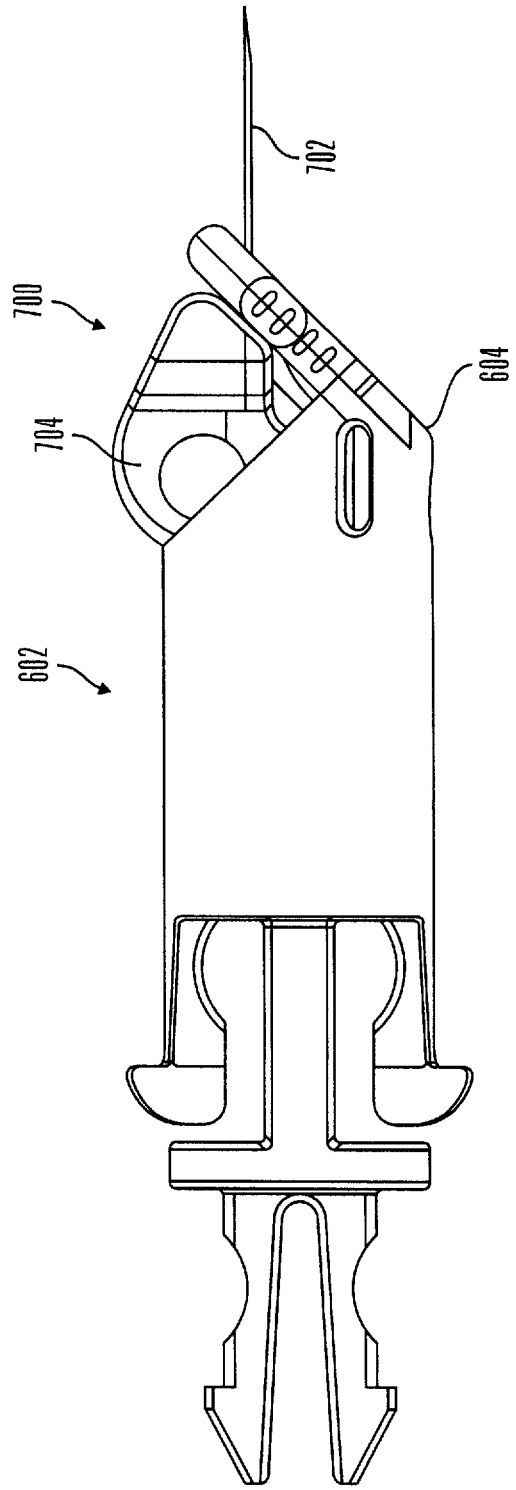
FIG. 44 is an enlarged side plan view of the one type of insertion set held in a carrier body of the insertion device shown in FIG. 41.

FIGS. 40a-40g illustrate one method of insertion of an insertion set 400 with the insertion device 500 in accordance with an embodiment of the present invention. The user first cleans and sterilizes an insertion site on the skin. Next, the user makes sure the insertion device 500 has the carrier body 504 in the advanced position to avoid unintentional activation of the insertion device 500 before placement on the skin. As shown in FIG. 40a, the user places the insertion set 400 in the cavity 514 of the carrier body by aligning the tubing (or wire leads or the like) with the slot 536 in the carrier body 504 and the slot 538 in the barrel 502 of the insertion device 500. The user presses against the piercing member guard 414 (or needle guard) to seat the piercing member hub 408 (or needle hub) and the insertion set 400 in the cavity 514 of the carrier body 504. As shown in FIG. 40b, the user removes the adhesive backing 416 covering the adhesive 406 on the rim 404 of the insertion set 400. It is preferred that the piercing member guard 414 is not removed at this point to avoid unintentional sticks by the piercing member 402, and minimize or avoid contact with the adhesive 406. As shown in FIG. 40c, the user presses against the piercing member guard 414 to move the carrier body 504 from the advance position to the retracted position, at which point the trigger buttons 510 and 512 will extend out of the portal openings 526 and 528 to extend beyond the guide channels 520 and 522 to lock the carrier body 504 in the retracted position. Next, as shown in FIG. 40d, the user removes the piercing member guard 414 (normally by twisting) to expose the piercing member 402 while maintaining the insertion set 400 within the carrier body 504. Then, as shown in FIG. 40e, the user places the surface seat 501 of the barrel 502 of the insertion device 500 with the insertion set 400 over the insertion site on the skin. The user depresses the two trigger buttons 510 and 512 through the portal openings 526 and 528 sufficiently for the trigger buttons 510 and 512 to slide down along the guide channels 520 and 522 to insert and install the insertion set 400 at the insertion site on the skin. As shown in FIG. 40f, the user depresses the release button 508 to release the insertion set from the cavity 514 of the carrier body 504. Finally, as shown in FIG. 40g, the user removes the insertion device 500, while maintaining installation of the insertion set 400. In alternative embodiments, the user may extend the release button 508 to lift off the piercing member hub 408 and piercing member 402, and maintain the remainder of the insertion set 400 at the insertion site on the skin. If the piercing member hub 408 and piercing member 402 are lifted off the device, the user should re-install the piercing member guard 414 prior to removal of the remaining set from the insertion device 500.

FIGS. 41-46 illustrate an insertion device 600 in accordance with a third embodiment that is similar to the insertion devices shown in FIGS. 1-34. The insertion device 600 includes a device housing end 601 and a carrier body 602 that has angled insertion contact surfaces 603 and 604. The angled insertion contact surfaces 603 and 604 enable the user to properly angle the insertion device 600 to insert an insertion set 700, or the like, at the proper insertion angle relative to the skin. An insertion set similar to the insertion set 700 is disclosed in U.S. patent application Ser. No. 08/871,831 (PCT Application Serial No. US98/10832) to Van Antwerp et al. entitled "Disposable Sensor Insertion Assembly" or an insertion set that can be inserted at an angle as disclosed in U.S. patent application Ser. No. 09/034,626 to Funderburk et al. entitled "Medication Infusion Set", both or which are herein incorporated by reference. Preferred embodiments of the insertion device 600 have angled insertion contact surfaces 603 and 604 that permit insertion of insertion sets, or the like, that are angled from 89.9 degrees to 25 degrees relative to the skin surface. In further embodiments, the angled insertion contact surfaces 603 and 604 may handle even shallower angles down to approximately 10 degrees relative to the skin surface.

The key is the angled insertion contact surfaces 603 and 604 mirrors the insertion angle of the insertion set 700, or the like, so that the piercing member 702 (or needle) of the insertion set 700, or the like, is in axial alignment in the direction of movement of the carrier body 602 of the insertion device 600. This permits an insertion device designed primarily for use with a 90 degree insertion set, or the like, to be modified to work with angled insertion sets 700, or the like, by modification of the angle of the angled insertion contact surfaces 603 and 604. In addition, it is preferred that the piercing member 702 of the insertion set 700, or the like, be slightly off-center from the center axis of the carrier body 602 to permit easy removal of the insertion device 600 once the insertion set 700, or the like, has been inserted. Preferred embodiments of the present invention include a carrier body 602 with a receiving structure that includes a recess 606 and bore 608 on one side of the carrier body 602. The recess 606 is adapted to hold the piercing member hub 704 by a slight interference fit and the bore 608 is adapted to hold the insertion tubing or transmitter hub 706 of the insertion set 700, or the like. In other embodiments for the insertion sets such as infusion sets with tubing (or sensor sets with wire leads already connected to a sensor) the bore 608 may be open on one side (not shown) to permit insertion and removal of the infusion tubing (or wire leads), but closed of sufficiently to securely hold and grasp the insertion tubing or transmitter hub 706 that connects the tubing or wire leads to the housing of the insertion set 700, or the like.

FIG. 47 illustrates an insertion device 800 that is adapted for inserting insertion sets, or the like, at angles that are generally less than or equal to 10 degrees relative to the skin surface after insertion of the insertion set, or the like. This embodiment includes a pair of pinchers 802 and 804 that grasps the skin. The pinchers 802 and 804 pinches (or bunches) up the skin in front of a carrier body 806 holding an insertion set, or the like. Once the skin is pinched (or bunched up), the user depresses an activation button and the insertion set, or the like, is inserted into the skin. In alternative embodiments, the user presses the pinchers 802 and 804 closer together to activate the insertion device 800. After insertion, the user releases the pinchers 802 and 804 and removes the insertion device 800 from the insertion set, or the like. The effect of this embodiment is to raise the skin so that the actual insertion angle of the piercing member relative to the side of the raised (or pinched) area of skin ranges from 10 degrees to 90 degrees so that the piercing member is inserted in manner similar to the embodiments described above. However, when the pinched skin is released, the piercing member is left in the skin at a shallow angle between 0 and 10 degrees. The amount of pinching and the height of the pinch must be carefully controlled to assure that the insertion set, or the like, is inserted at the proper depth and location in the skin tissue. One example of an insertion set that can be inserted at an angle as disclosed in U.S. patent application Ser. No. 09/034,626 to Funderburk et al. entitled "Medication Infusion Set", which is herein incorporated by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An insertion device for inserting at least a portion of at least one piercing member through the skin of a patient, the insertion device comprising:
    a device housing;
    a carrier body slidably received within the device housing for movement between an advanced position and a retracted position, the carrier body including a receiving structure to support an insertion set in a position with the at least one piercing member oriented for insertion through the skin of the patient at a predetermined angle relative to the skin of the patient upon movement of the carrier body from the retracted position to the advanced position, wherein the carrier body is shipped with the insertion set pre-installed; and
    a driver operatively coupled between the device housing and the carrier body to urge, upon actuation of a first trigger and a second trigger, the carrier body with a controlled force and speed from the retracted position toward the advanced position to place at least a portion of the at least one piercing member through the skin of the patient to install the insertion set to the patient, wherein the receiving structure of the carrier body is removable from the insertion set while maintaining installation of the insertion set to the patient, and the insertion set is left on the skin of the patient without the piercing member by removing the insertion device from the skin of the patient, the insertion device being engaged to the at least one piercing member to withdraw the at least one piercing member from the insertion set.

2. An insertion device according to claim 1, wherein the at least one piercing member is separable from the carrier body.

3. An insertion device according to claim 1, wherein the at least one piercing member extends through a cannula of the insertion set.

4. An insertion device according to claim 1, wherein the predetermined angle relative to the skin is about 90 degrees, or is between 90 degrees and 10 degrees.

5. An insertion device according to claim 1, wherein the predetermined angle relative to the skin is between 0 degrees and 10 degrees after insertion.

6. An insertion device according to claim 1, wherein the insertion set is one of a transcutaneous insertion set, and a subcutaneous insertion set.

7. An insertion device according to claim 1, wherein the insertion set either rests mainly on the surface of the skin after insertion, or is implanted in the skin of the patient after insertion.

8. An insertion device according to claim 1, wherein the at least one piercing member is one of a needle, and a plurality of needles, or the at least one piercing member are microneedles.

9. An insertion device according to claim 1, wherein the insertion set is an infusion set, or a sensor set, or both an infusion set and sensor set combined into an integral unit.

10. An insertion device according to claim 1, wherein the device housing has a forward end defining a generally planar angled insertion contact surface for placement against the patient's skin with the device housing in a predetermined orientation relative to the patient's skin that mirrors the predetermined angle relative to the patient's skin.

11. An insertion device according to claim 1, wherein the driver includes at least one spring for spring-loaded movement of the carrier body from the retracted position to the advanced position.

12. An insertion device according to claim 1, wherein the driver includes a force changing mechanism that permits alteration of the controlled force and speed of the carrier body moving from the retracted position to the advanced position from one insertion cycle to another insertion cycle.

13. An insertion device according to claim 1, wherein the device housing and the carrier body include a cooperatively engageable track mechanism for guiding movement of the carrier body between the advanced and retracted positions while retaining the carrier body against rotation relative to the device housing.

14. An insertion device according to claim 1, wherein the insertion device engages a hub of the at least one piercing member to withdraw the at least one piercing member from the insertion set.

* * * * *